(12) United States Patent
Yang et al.

(10) Patent No.: US 9,014,784 B2
(45) Date of Patent: Apr. 21, 2015

(54) RECONFIGURABLE MRI-GUIDED SURGICAL APPARATUS

(71) Applicants: Xiaoyu Yang, Indiana, PA (US); Tsinghua Zheng, Aurora, OH (US); Shinya Handa, Mayfield Village, OH (US)

(72) Inventors: Xiaoyu Yang, Indiana, PA (US); Tsinghua Zheng, Aurora, OH (US); Shinya Handa, Mayfield Village, OH (US)

(*) Notice: Subject to any disclaimer, the term of this patent is extended or adjusted under 35 U.S.C. 154(b) by 268 days.

(21) Appl. No.: 13/670,224

(22) Filed: Nov. 6, 2012

(65) Prior Publication Data

US 2014/0128723 A1 May 8, 2014

(51) Int. Cl.
| | | |
|---|---|---|
| *A61B 5/05* | (2006.01) | |
| *A61B 5/055* | (2006.01) | |
| *A61B 10/02* | (2006.01) | |
| *A61B 5/00* | (2006.01) | |
| *A61B 19/00* | (2006.01) | |

(52) U.S. Cl.
CPC ........... *A61B 5/0555* (2013.01); *A61B 10/0233* (2013.01); *A61B 5/4312* (2013.01); *A61B 19/201* (2013.01); *A61B 2019/205* (2013.01); *A61B 2019/5236* (2013.01)

(58) Field of Classification Search
None
See application file for complete search history.

(56) References Cited

U.S. PATENT DOCUMENTS 7,711,407 B2 *   5/2010   Hughes et al. ................ 600/417
7,970,452 B2 *   6/2011   Piron et al. ................... 600/411

* cited by examiner

*Primary Examiner* — Unsu Jung
*Assistant Examiner* — Joseph M Santos Rodriguez

(57) ABSTRACT

Apparatus associated with improved magnetic resonance imaging (MRI) guided needle biopsy procedures (e.g., breast needle biopsy) are described. One example apparatus includes a support structure configured to support a patient in a face-down prone position where a breast of the patient is positioned in a first free hanging pre-imaging position. The example apparatus includes an immobilization structure configured to reposition the breast into an immobilized position suitable for MRI and for medical instrument access. The immobilization structure may include a biopsy plate, a pressure plate, and MRI coils. The MRI coils are configured to be repositioned from a first position associated with the free hanging pre-imaging position to a second position associated with the immobilized position to facilitate improving the signal to noise ratio associated with signal received from the breast through the MRI coils. The biopsy plate is removable without removing either of the MRI coils.

15 Claims, 39 Drawing Sheets

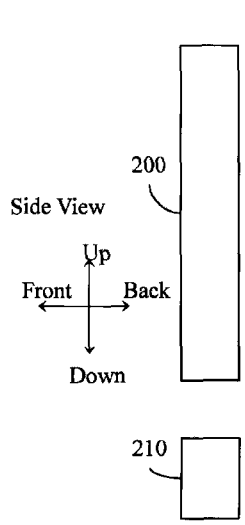
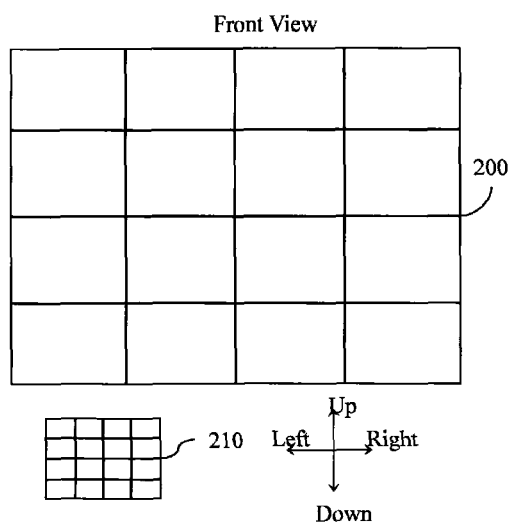
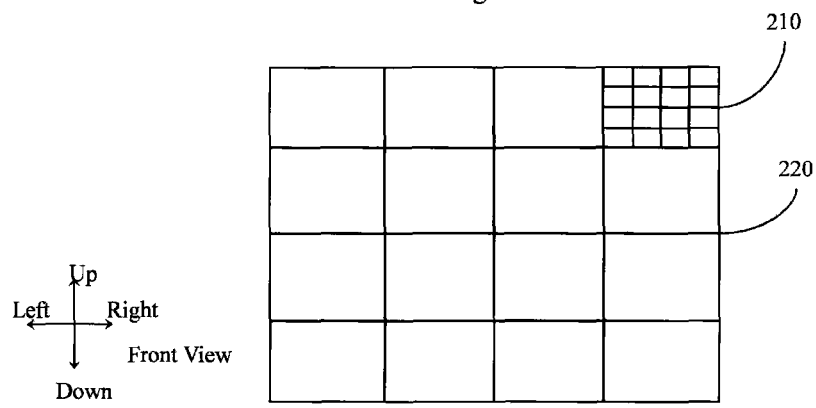
Figure 2b
Figure 2a
Figure 2c

3800

Front View

US 9,014,784 B2

RECONFIGURABLE MRI-GUIDED SURGICAL APPARATUS

BACKGROUND

Many patents have issued on breast specific coils for magnetic resonance imaging (MRI). See, for example, U.S. Pat. Nos. 7,084,631 and 7,970,452. Some of these breast specific coils are designed to improve imaging by increasing signal-to-noise ratio (SNR) by adding coils or by facilitating repositioning coils. Some of these breast specific coils are suitable for MRI-guided surgical procedures.

These conventional breast specific coils include plates that can be moved to immobilize a breast and some even include coils that can be added or removed. Some conventional breast specific coils include center supports that may include RF coils for bilateral imaging. While these conventional breast specific coils have improved breast imaging and have improved MRI-guided procedures, further improvements are still sought.

MRI detects the nuclear magnetic resonance (NMR) signals produced by protons in the presence of a strong magnetic field after specific excitation by radio frequency (RF) energy. The NMR signals are detected by antennae known as "coils." In different usages, the term "coil" may refer to just the antenna, or may refer to the antenna, its housing, and support structure. The term "coil" may refer to an assembly that includes two or more coils. An operable part of the coil may be referred to as a "coil element." The operable part may also be referred to as the coil.

MRI involves sampling in k-space to acquire an NMR signal from an object exposed to magnetic fields, gradients, and RF energy produced by an MRI apparatus. The quality of a magnetic resonance image may depend, at least in part, on the proximity of the apparatus (e.g., coils) producing the fields, gradients, and RF energy to which the object being imaged is subjected. The quality may also depend on the number, proximity, and orientation of coils receiving NMR signals from an object. MRI is frequently used for diagnostic medical imaging.

Recently, MRI has also been used to guide surgical techniques. For example, MRI has been used to guide needle biopsies.

The quality of the NMR signal received from an object being imaged may be described, at least in part, by its SNR. One goal in an MRI session is to have a good (e.g., high) SNR. SNR is a function of several factors. One of the factors includes how close a coil is located to the object being imaged. Theoretically, a separate individual coil could be fashioned for each MRI session to account for differences between patients. Practically, this is unlikely due to both time and cost constraints. Therefore, one-size-fits-all coils are generally employed, or a very small set of different sized coils (e.g., adult, child) may be employed. Unfortunately, one-size-fits-all coils generally yield poor (e.g., low) SNR. Additionally, the need to accommodate access to a breast for an interventional device (e.g., biopsy needle) may also produce a competition between proximity for high SNR and spacing to allow access.

Breast MRI has become increasingly important over time. Thus, numerous patents have been issued in this space. For example, U.S. Pat. No. 7,084,631 describes an MRI array coil system for breast imaging. The coil system includes top and bottom openings for receiving and supporting breasts, and side windows for accessing the breasts from the side while the patient is positioned on the apparatus.

By way of further illustration, U.S. Pat. No. 7,970,452 describes an open architecture imaging apparatus and coil system for MRI. The '452 patent describes an apparatus where RF coils and compression plates can be positioned, repositioned, held in place, and otherwise manipulated to provide improved SNR and an improved patient experience. The '452 patent describes a separable and reconfigurable coil system that may be optimized for particular imaging purposes including, but not limited to, bilateral imaging, unilateral imaging, imaging of the chest wall for mastectomy patients, and interventional procedures. The '452 patent recites that "a fundamental aspect to this disclosure of technology is the separation of patient support structures from RF coil system." (Column 7, lines 18-20). The '452 patent also recites how "the ability to accept modular coil elements in an interchangeable support structure is a unique aspect of the present invention." (Column 10, lines 64-66). Thus, some patents have described modular coil elements that can be added or removed from a larger patient support structure.

Some conventional apparatus exist that employ the one-size-fits-all approach for supporting needle biopsies for acquiring breast tissue. The one-size-fits-all approach to coil design for breast imaging may lead to sub-optimal results. Conventional apparatus may include a coil and a biopsy plate.

FIG. 1a illustrates a front view of a coil 100. FIG. 1b illustrates a side view of coil 100. Coil 100 includes a housing 110 and an operational part 120. The operational part 120 may include copper wire or traces and attached circuitry. The wire and the circuitry may be configured to operate as a transceiver that can both transmit RF energy into an object to be imaged or can receive NMR signals resulting from the application of that RF energy. How close the copper wire can be placed to an object to be imaged is a function of at least the thickness T1 of the housing 110. Conventionally, coil 100 has been a monolithic item that can be positioned or manipulated as a single item.

FIG. 2a illustrates a front view of a biopsy plate 200. FIG. 2b illustrates a side view of biopsy plate 200. FIG. 2c illustrates a front view of another biopsy plate 220. Biopsy plate 200 is illustrated being divided into sixteen regions. These regions may be fashioned by internal dividers. Biopsy plate 200 may be made, for example, from plastic. During a surgical procedure (e.g., biopsy), biopsy plate 200 is likely going to come in contact with biological fluids (e.g., blood). Therefore a separate biopsy plate 200 will likely be employed for each biopsy and the biopsy plate 200 will likely be discarded after use.

The sixteen regions may measure, for example, one inch by one inch. A needle biopsy may need greater precision for positioning a needle than can be provided by a one inch by one inch opening. Therefore, a needle positioning block 210 may be positioned in one of the sixteen regions. The needle positioning block 210 is also illustrated with sixteen regions. While sixteen regions are illustrated in both biopsy plate 200 and needle positioning block 210, different numbers of regions may be found in different biopsy plates and in different needle positioning apparatus. In second biopsy plate 220, one of the regions houses the needle positioning block 210. In a needle biopsy, the needle would be inserted to a desired depth into a volume (e.g., breast) after a location within the volume was identified during imaging. The position and direction of travel of the needle is controlled by the region in the needle positioning block 210 through which the needle is inserted. Both the biopsy plate 200 and the needle positioning block 210 are likely to be discarded after a procedure.

FIG. 3 illustrates a side view of a coil 300 paired with a biopsy plate 310. Coil 300 includes an operational part 301 and a housing 302. The biopsy plate 310 is illustrated with a needle positioning block 311 housed in one of the regions in biopsy plate 310. During the image acquisition portion of an MRI-guided needle biopsy, the coil 300 and the biopsy plate 310 may be positioned close together and as close to a breast as possible. How close the coil 300 can be placed to the volume to be imaged depends on the thickness T3 of the housing of the coil 300 and the thickness T4 of the biopsy plate 310. When the imaging portion of the MRI-guided needle biopsy is complete, the coil 300 may be removed to provide access to the biopsy plate 310 and then the needle positioning block 311 may be inserted into the biopsy plate 310 at a relevant location.

A biopsy plate is likely to come in contact with biological fluid during a biopsy. Therefore, it is likely that the biopsy plate will need to be destroyed after use. Coils are expensive. Coils are also generally housed in a solid housing. Therefore, it is unlikely that a needle will be pushed through a coil, both because it would damage the coil and because it would be undesirable to have the coil come in contact with the biological fluid. Therefore, during an MRI-guided biopsy, the coil may first be positioned beside the biopsy plate to facilitate acquiring an image and registering the image to the biopsy plate, and then, after the image is acquired, the coil may be removed so that the needle can be pushed through the biopsy plate. Positioning the coil and then removing the coil requires skilled operator attention, and thus takes time. Also, as described above, how close the coil is positioned to the volume to be imaged impacts the SNR for signal acquired from the object being imaged. In general, having the coil closer to the volume during an MRI procedure improves SNR while having the coil farther from the volume negatively impacts SNR.

SNR may also depend on the number of coils and the orientation of the coils used to image a volume. The anatomy of a volume to be imaged may control both the number of coils that can be used and the proximity of those coils. For example, it is possible to surround a knee with a number of coils and to bring those coils into very close proximity with the knee. However, for an image guided needle biopsy of a breast, it may not be possible to surround the volume and it may not be possible to bring the coils as close to the volume as desired due to the requirement of fixing the volume with the biopsy plate.

FIG. 4a illustrates a view looking towards the feet from the head of a patient of portions of an apparatus 405. FIG. 4b illustrates a top view of apparatus 405. Apparatus 405 may support a patient who is lying face down during an MRI-guided needle biopsy. Apparatus 405 includes housing 410, a biopsy plate 420, and a central fixed element 430. Apparatus 405 includes an opening 499 through which breast 400 may hang. Apparatus 405 may be configured with two such openings.

FIG. 4a also represents a breast 400 as it might appear when viewed from the head of a patient that is lying face down on apparatus 405. Initially, the breast 400 would hang down through opening 499 in the apparatus 405. In the initial positioning, breast 400 might be able to move, making it difficult, if even possible at all, to accurately place a needle into a region of interest identified during an MRI-guided biopsy. Therefore, before imaging, the breast 400 may be compressed into a different shape by being squeezed between biopsy plate 420 and another fixed element 430.

FIG. 5a illustrates a view looking towards the feet from the head of a patient of portions of an apparatus 505. FIG. 5b provides a top view of apparatus 505. Apparatus 505 may support a patient who is lying face down using support structure 510. Apparatus 505 includes a biopsy plate 520 and a central fixed element 530. Apparatus 505 includes an opening 599 through which breast 500 may hang. Apparatus 505 may be configured with two such openings.

FIG. 5a also represents breast 500 as it might appear when viewed from the head of a patient that is lying face down on apparatus 505. The breast 500 is illustrated after it has been compressed between biopsy plate 520 and fixed element 530. A coil 540 is illustrated beside biopsy plate 520. The breast 500 would be imaged using coil 540. Other coils may also be involved in imaging breast 500. Note that as biopsy plate 520 compresses breast 500, breast 500 is moved farther from coil 540. With the breast 500 compressed into a shape that can be maintained during imaging and then during needle insertion, the imaging may proceed.

FIG. 6 illustrates breast 500 as it might appear when viewed from the head of a patient that is lying face down on apparatus 505. The breast 500 is illustrated after a region of interest 550 has been identified. A needle 560 may be inserted through the biopsy plate 520 to acquire tissue from the region of interest 550. A needle positioning block may be positioned in the biopsy plate 520 before the needle 560 is inserted to facilitate more accurate placement of the needle 560.

Conventionally, the coil 540 is removed before the needle 560 is inserted into the region of interest 550. While an MRI-guided needle biopsy could be performed using the apparatus illustrated in FIGS. 5 and 6, additional coils and improved positioning of those coils could lead to improved imaging through improved SNR. Additionally, improvements to coil 540 may facilitate improved operator handling and thus reduced procedure time. Improved SNR, improved imaging, and improved operator handling may yield more accurate MRI-guided needle biopsies.

BRIEF DESCRIPTION OF THE DRAWINGS

The accompanying drawings, which are incorporated in and constitute a part of the specification, illustrate various example systems, apparatus, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

FIGS. 2a, 2b, and 2c illustrate a biopsy plate.

DETAILED DESCRIPTION

Figure 1A:
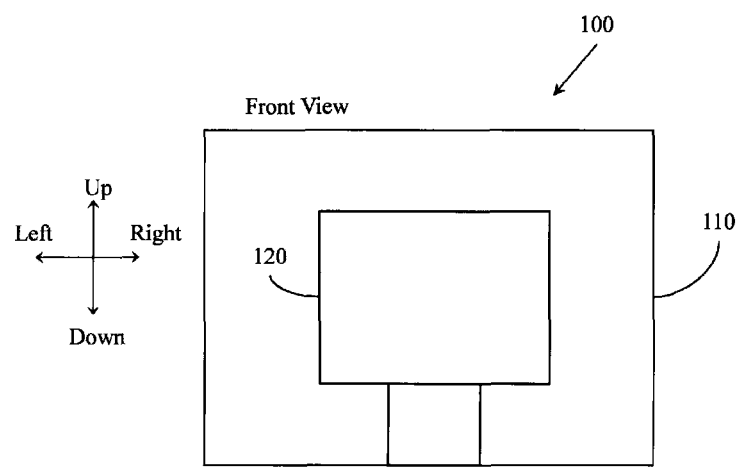
FIGS. 1a and 1b illustrate an MRI coil.
Figure 1B:
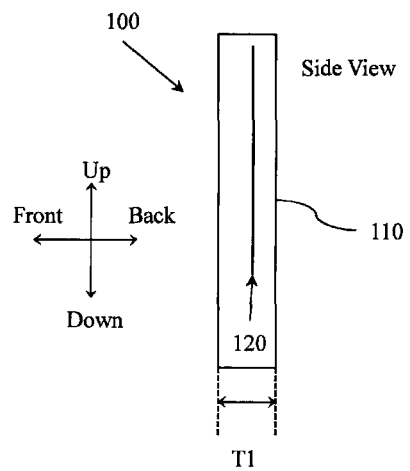
Figure 3:
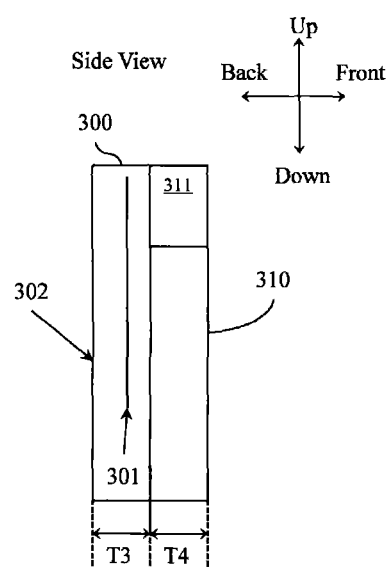
FIG. 3 illustrates an MRI coil paired with a biopsy plate.
Figure 4A:
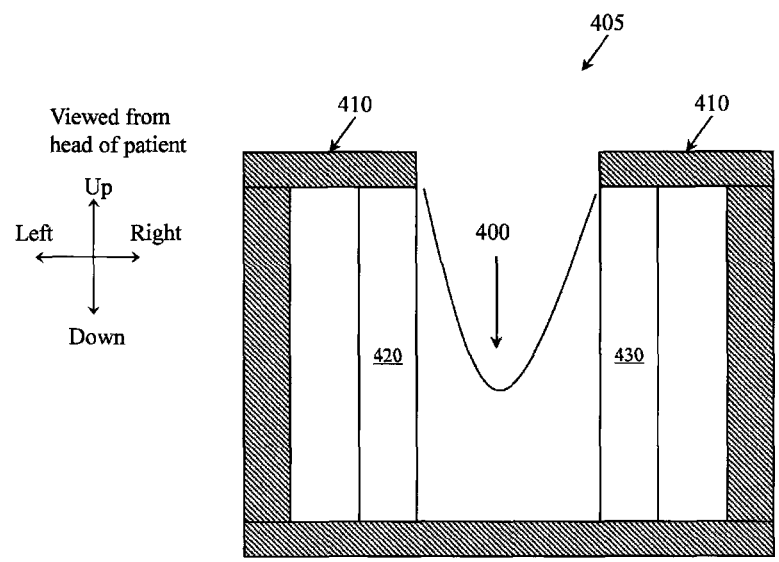
FIGS. 4a and 4b illustrate a portion of an MRI-guided surgical apparatus.
Figure 4B:
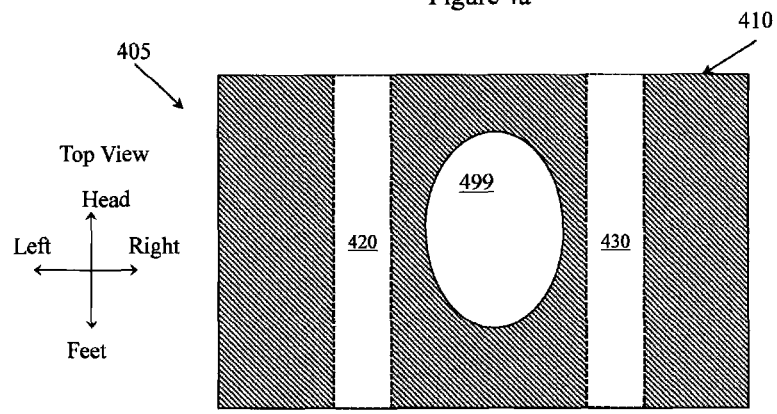
Figure 5A:
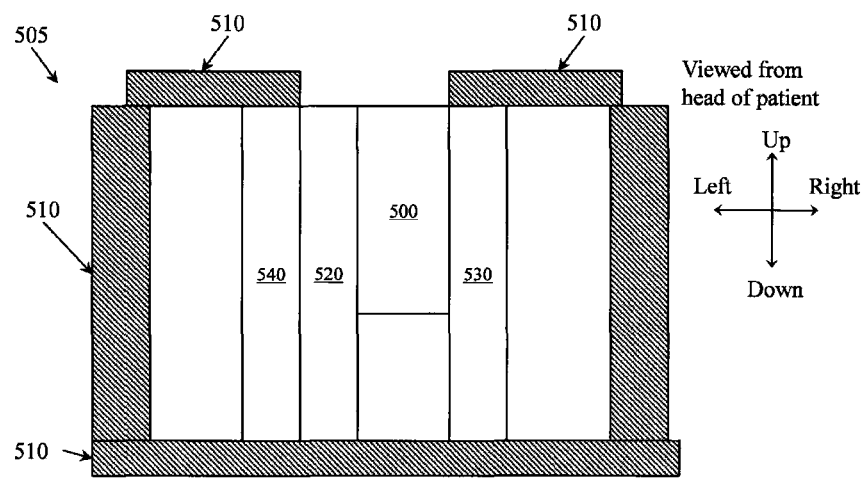
FIGS. 5a and 5b illustrate a portion of an MRI-guided surgical apparatus.
Figure 5B:
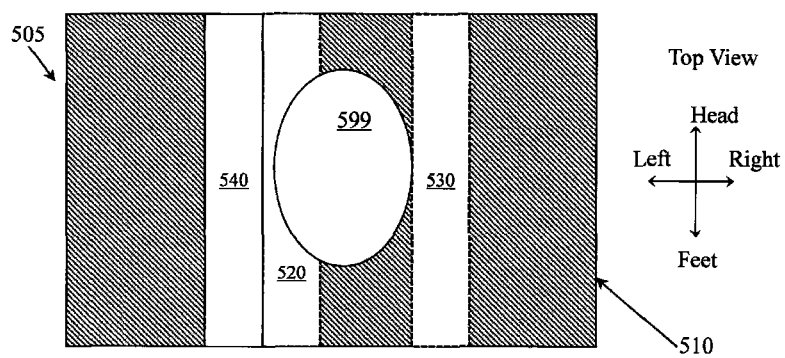
Figure 6:
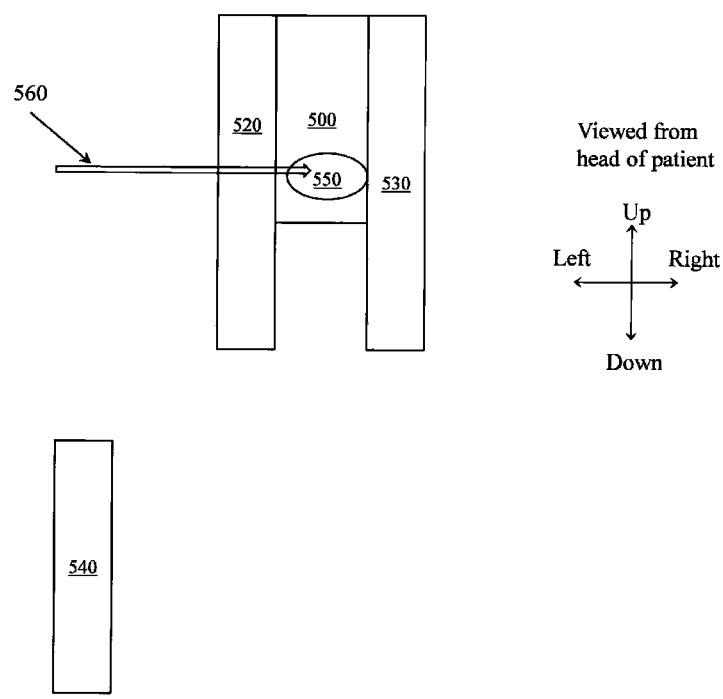
FIG. 6 illustrates a portion of an MRI-guided surgical apparatus.

Example apparatus described herein concern a reconfigurable MRI-guided surgical apparatus for supporting MRI-guided surgical procedures. Example apparatus provide additional coils, provide coils that may be repositioned to facilitate placing a coil closer to a volume to be imaged, provide attachments that facilitate reconfiguration by moving coils out of the way without requiring removing the coils, provide a center coil that can be rotated from a bilateral imaging mode to a unilateral high resolution imaging mode, and facilitate reducing operator actions required to reposition a coil to gain access to a medical instrument guidance assembly.

Example apparatus accept a modular medical instrument guidance assembly that may be inserted, used, and then removed from a larger supporting apparatus without requiring removal of other parts (e.g., coils). One example surgical procedure is a needle biopsy and thus one example medical instrument guidance assembly is a biopsy plate. Other surgical procedures may include, but are not limited to, a trans-cannula procedure, cryoablation, laser ablation, hyperthermia, medicament delivery, percutaneous removal of a lesion, cyst, or other item, and percutaneous draining of a lesion, cyst, or other item.

Example apparatus include an inner assembly that may be housed, placed in, or otherwise associated with a larger breast coil apparatus. An example inner assembly may have one or more guides and one or more attachment points for biopsy plates that facilitate making the biopsy plates movable and/or lockable. An example inner assembly may also have one or more guides, one or more attachment points, and one or more hinges for side coils that facilitate making the side coils movable, lockable, and/or able to be swung away from a related biopsy plate. An example inner assembly may also have one or more guides, attachment points, and hinges for a center assembly that facilitate making the center assembly movable, lockable, and/or able to be rotated from positions including a horizontal orientation to a vertical orientation. An example inner assembly facilitates moving biopsy plates towards and away from a breast to facilitate immobilizing a breast to be imaged. An example inner assembly also facilitates moving side coils towards and away from the breast to bring the side coils to a desired proximity for imaging the breast. Since side coils may partially block access to a biopsy plate, an example inner assembly may also facilitate repositioning side coils without removing them from inner volume assembly. Repositioning a side coil may provide access to a biopsy plate. An example inner assembly may also facilitate rotating a center coil from an upright position used for bilateral imaging to a horizontal position used for unilateral imaging. Being able to rotate a center coil to a position beneath a breast may increase the number of coils available for imaging and may also facilitate quadrature imaging by orienting the center coil perpendicular to a side coil. In quadrature reception, NMR signals are detected in two orthogonal directions by two independent coils that cover the same volume of interest.

Figure 7:
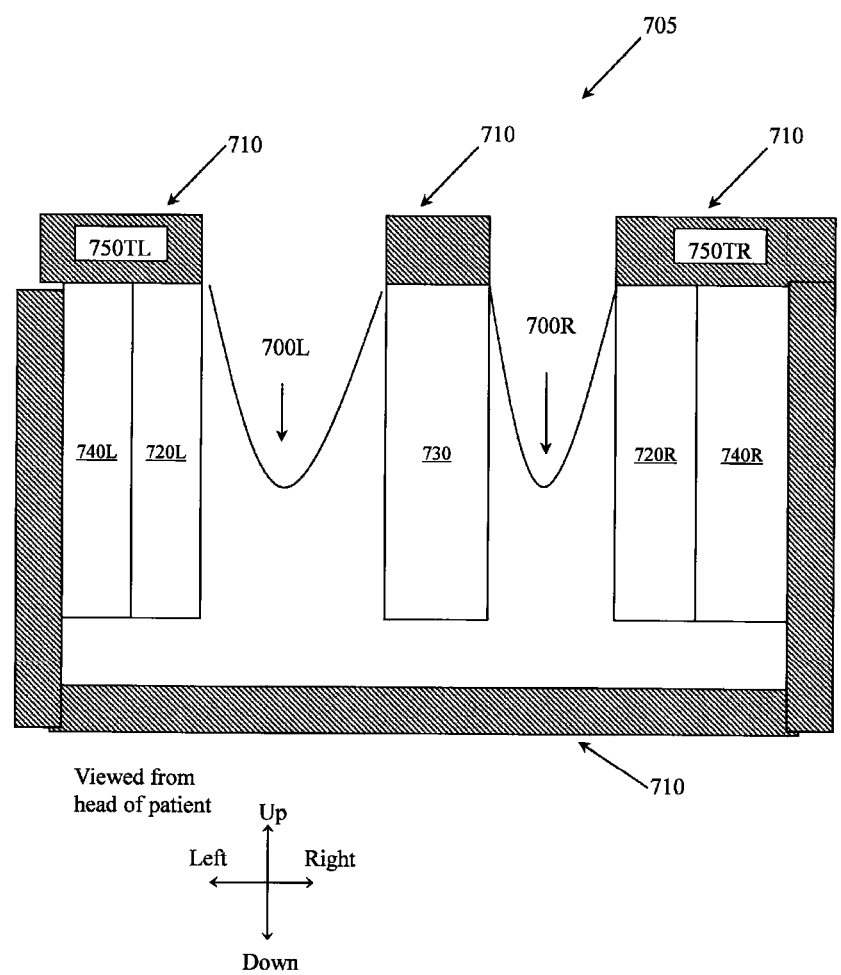
FIG. 7 illustrates a portion of an example reconfigurable MRI-guided surgical apparatus.
Figure 24:
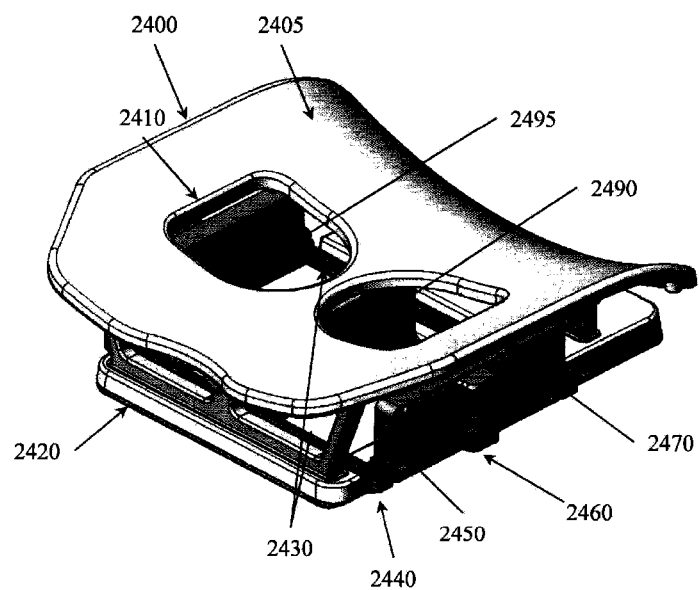
FIG. 24 illustrates an example reconfigurable MRI-guided surgical apparatus.

FIG. 7 illustrates portions of an apparatus 705 that may support a patient who is lying face down during an MRI-guided needle biopsy. FIG. 24 illustrates one example larger structure (e.g., breast coil apparatus 2400) with which apparatus 705 may be used. Apparatus 705, and other embodiments described herein, facilitate imaging a patient's breast to localize an area of interest in the breast. Apparatus 705, and other embodiments described herein, also facilitate readily and accurately obtaining a sample from the breast using a medical instrument (e.g., needle). The medical instrument may be guided by a medical instrument guidance assembly (e.g., biopsy plate). Accurate placement and acquisition may depend on adequate registration between the breast and the medical instrument guidance assembly.

Apparatus 705 is viewed from the head of the patient looking towards the feet of the patient. Apparatus 705 includes support structure 710 and two biopsy plates: a left biopsy plate 720L, and a right biopsy plate 720R. Apparatus 705 also includes two side coils: a left side coil 740L, and a right side coil 740R. Apparatus 705 also includes a central element 730 that may be used in compressing a breast. For example, left breast 700L may be compressed against central element 730 by moving left biopsy plate 720L towards the central element 730. Unlike conventional systems, when biopsy plate 720L is moved towards central element 730, left coil 740L may also be moved in with plate 720L. In one embodiment, coil 740L may be attached to plate 720L and they may move as a single unit. In another embodiment, coil 740L and plate 720L may be moved independently.

Apparatus 705 includes openings through which left breast 700L and right breast 700R of the patient may hang. Apparatus 705 may also include top coils and bottom coils. For example, apparatus 705 may include a left top coil 750TL and a right top coil 750TR. While two top coils are illustrated, a greater or lesser number of top coils could be employed.

Configuring apparatus 705 with the additional coils 750TL and 750TR may facilitate improving SNR in an MRI-guided needle biopsy both by increasing the number of coils available for imaging and by placing coils closer to the volume being imaged. However, note that as breast 700L is compressed by plate 720L towards element 730, breast 700L may be moved farther away from top left coil 750TL.

More generally, apparatus 705 is configured with a removable medical instrument guidance assembly, a coil, and structure for immobilizing the breast to facilitate registering a region of interest in the breast with the medical instrument guidance assembly.

Figure 8:
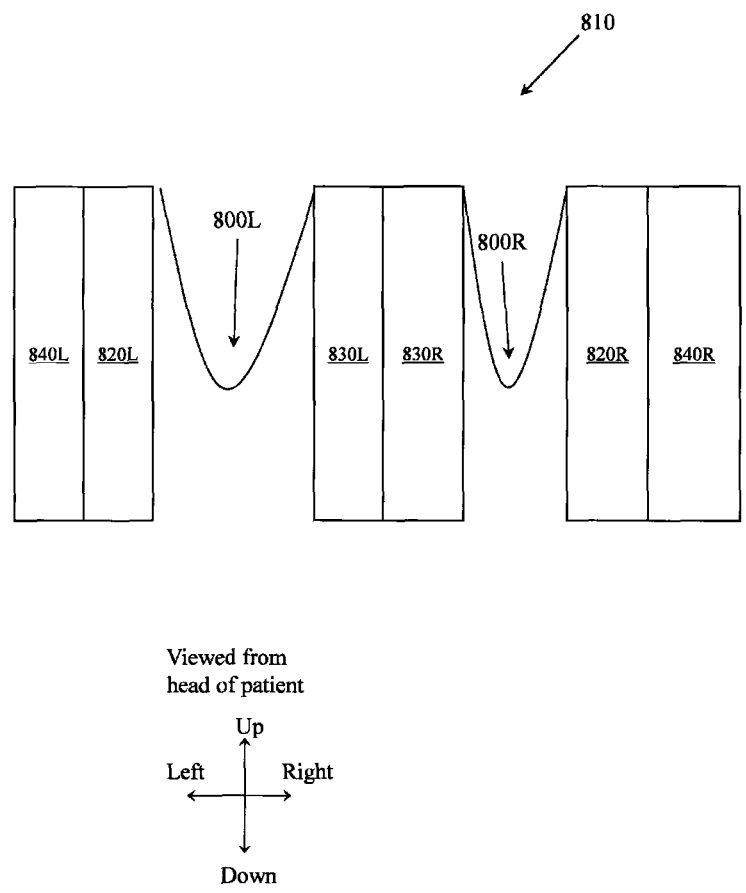
FIG. 8 illustrates a portion of an example reconfigurable MRI-guided surgical apparatus.

FIG. 8 illustrates portions of an apparatus 810 that may support a patient who is lying face down during an MRI-guided needle biopsy. Fixed support structures are not illustrated to facilitate focusing on the movable pieces. Apparatus 810 is viewed from the head of the patient looking towards the feet of the patient. Apparatus 810 includes two biopsy plates: a left biopsy plate 820L and a right biopsy plate 820R. Apparatus 810 also includes two side coils: a left side coil 840L and a right side coil 840R. Apparatus 810 also includes two central coils (830R, 830L) that may, in addition to being used for imaging, also perform the function of central element 730 (FIG. 7). Apparatus 810 includes openings through which left breast 800L and right breast 800R of the patient may hang. Having the breasts hang down allows gravity to draw the breasts down, which may facilitate accessing areas of interest within a patient's breast near the chest wall. Apparatus 810 may also include top coils and bottom coils.

Configuring apparatus 810 with the additional coils 830L and 830R may facilitate improving SNR in an MRI-guided needle biopsy both by increasing the number of coils available for imaging and by placing coils closer to the volume being imaged. In one embodiment, coils 830L and 830R may be replaced by a single coil. As breast 800L is compressed towards coil 830L by plate 820L, breast 800L is positioned closer to coil 830L, which may improve image quality. Additionally, coil 840L may be repositioned to remain beside plate 820L as plate 820L is moved towards coil 830L to compress breast 800L. This mitigates issues associated with conventional systems where the coils were fixed and could not move.

Figure 9:
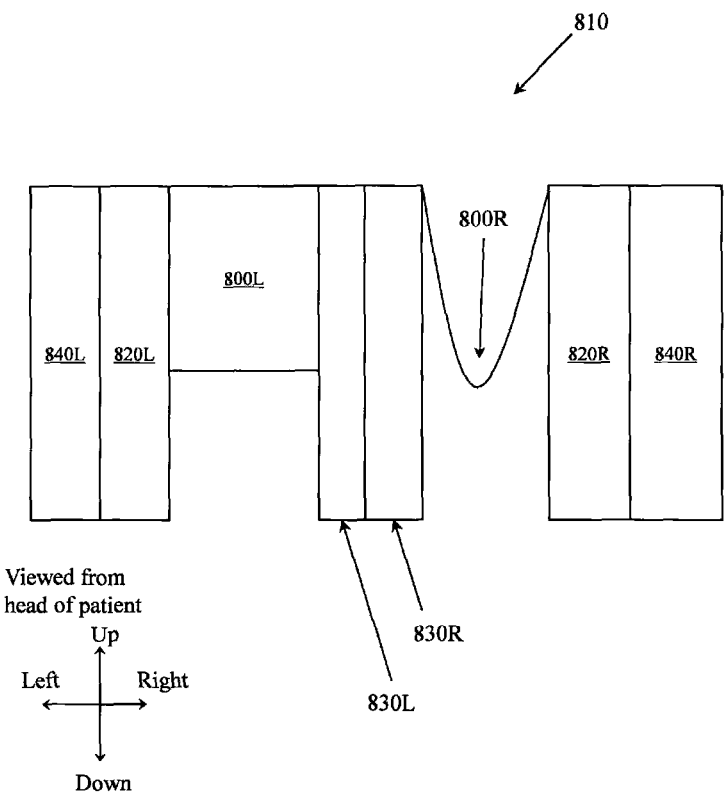
FIG. 9 illustrates a portion of an example reconfigurable MRI-guided surgical apparatus.

FIG. 9 illustrates portions of apparatus 810 after the left side biopsy plate 820L has been moved towards the left center coil 830L. Breast 800L has been compressed by the squeezing action of plate 820L and coil 830L. Compressing breast 800L facilitates holding breast 800L in a shape and position where a region of interest can be registered to a region in a biopsy plate. Registering a region of interest to a region in a biopsy plate means establishing a fixed spatial relationship between the two regions that will be maintained within a tolerance so long as the breast is held in the compressed state. Holding the breast in a fixed shape and position facilitates accurately inserting a needle into a region of interest. Compressing breast 800L also facilitates positioning left side coil 840L closer to the interior of the breast and positioning coil 830L closer to breast 800L.

Figure 10:
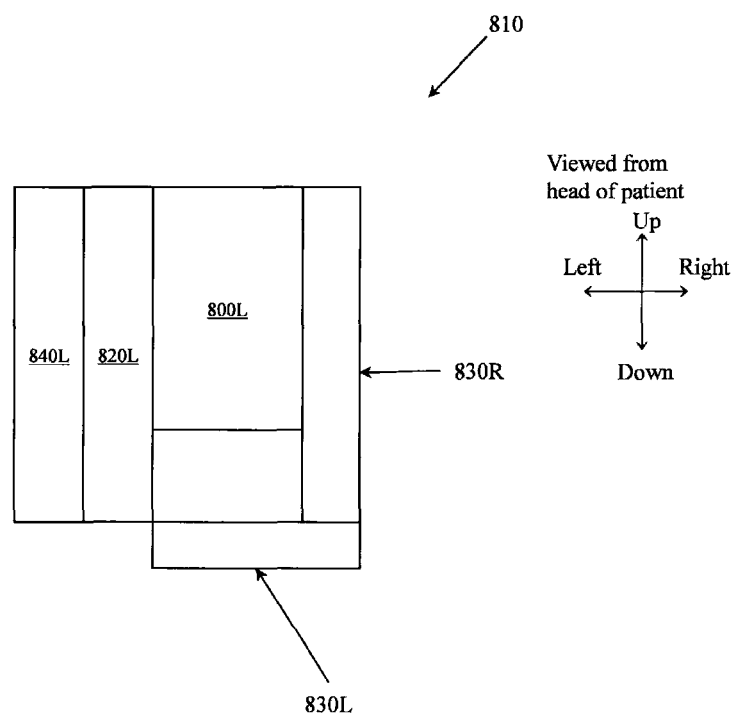
FIG. 10 illustrates a portion of an example reconfigurable MRI-guided surgical apparatus.

FIG. 10 illustrates portions of apparatus 810 after the left center coil 830L has been repositioned below left breast 800L. Left breast 800L has been compressed by moving left biopsy plate 820L towards right center coil 830R. In this configuration, apparatus 810 now provides three coils in close proximity to left breast 800L. Right center coil 830R is touching one side of breast 800L, left side coil 840L is closest to another side of breast 800L and left center coil 830L is positioned below breast 800L. Therefore, there are three coils positioned as close as practically possible to breast 800L. This may facilitate improving SNR which in turn may facilitate improving image quality. Having 830L perpendicular to 820L and 830R may also facilitate improving SNR by allowing for quadrature imaging. Coil 830L may be configured with a hinge or other connector that facilitates repositioning 830L from its initial vertical orientation to a subsequent horizontal position. While coil 830L is illustrated in a horizontal position, other orientations may be employed. While FIG. 9 illustrates two center coils 830L and 830R, in some embodiments there would only be a single center coil. In some embodiments where there are two center coils, only one coil may be used at a time.

Figure 11:
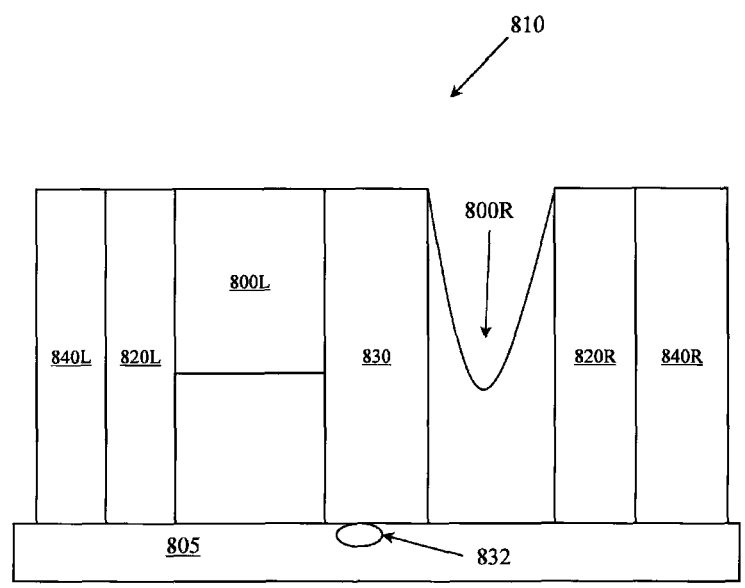
FIG. 11 illustrates a portion of an example reconfigurable MRI-guided surgical apparatus.
Figure 11:
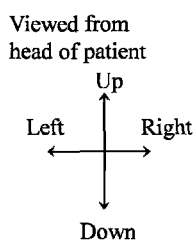

FIG. 11 illustrates another embodiment of portions of apparatus 810. In this embodiment, rather than having two central coils 830L and 830R, there is just a single central coil 830. Apparatus 810 may include a guide 805. Coil 830 may be attached to guide 805 by, for example, a hinge 832 or other connector that allows coil 830 to rotate from a vertical orientation to a horizontal orientation. While rotating coil 830 is described, more generally coil 830 can be repositioned from one position to another to facilitate keeping coil 830 in a position that contributes to improving SNR.

Figure 12:
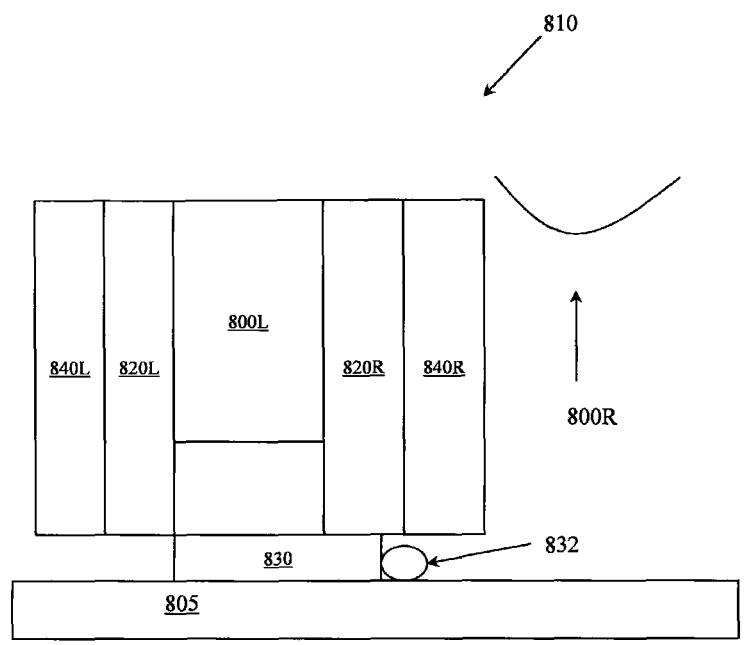
FIG. 12 illustrates a portion of an example reconfigurable MRI-guided surgical apparatus.
Figure 12:
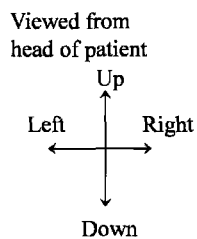

FIG. 12 illustrates portions of apparatus 810 after the central coil 830 has been repositioned below breast 800L. Breast 800R has been displaced upwards to allow right biopsy plate 820R and right side coil 840R to be moved into the center region. Breast 800L is illustrated being compressed between left biopsy plate 820L and right biopsy plate 820R.

Figure 13:
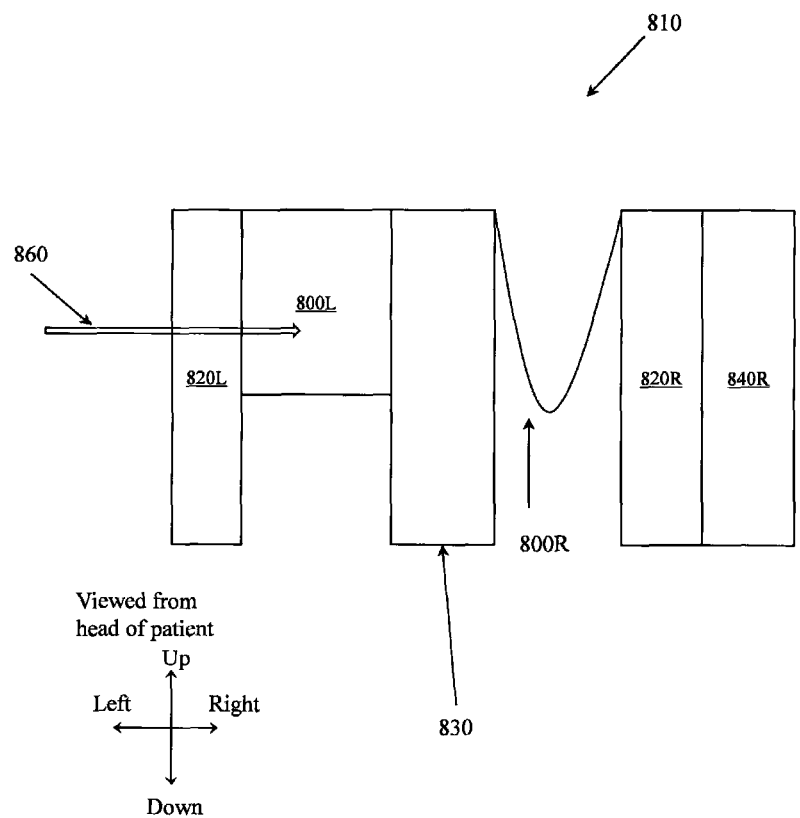
FIG. 13 illustrates a portion of an example reconfigurable MRI-guided surgical apparatus.

FIG. 13 illustrates a needle 860 being inserted laterally into breast 800L. To insert the needle 860 laterally, the left side coil 840L has been repositioned.

Figure 14:
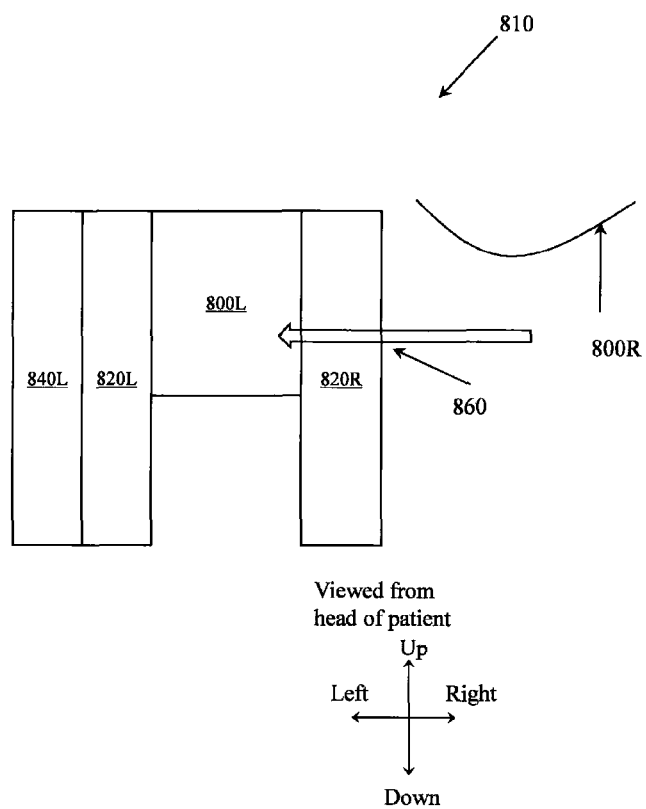
FIG. 14 illustrates a portion of an example reconfigurable MRI-guided surgical apparatus.
Figure 15:
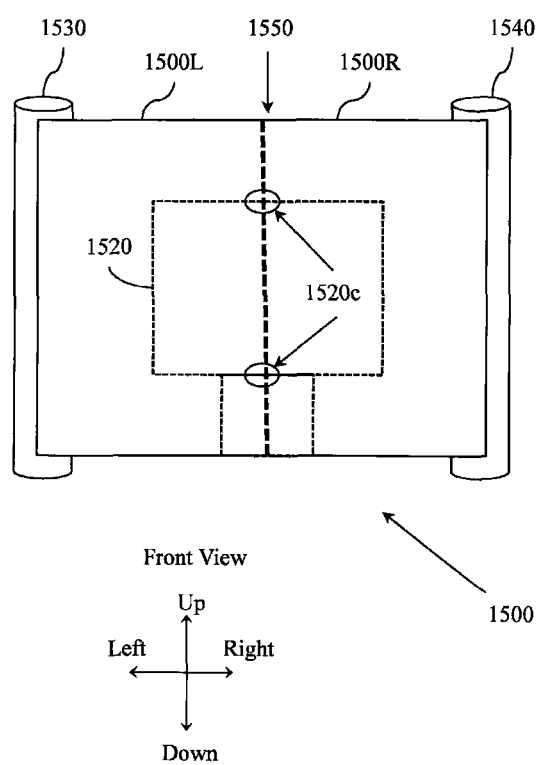
FIG. 15 illustrates a portion of an example reconfigurable MRI-guided surgical apparatus.

FIG. 14 illustrates needle 860 being inserted medially into breast 800L. To insert the needle 860 medially, the right side coil 840R may be repositioned or center coil 830R may be repositioned. Example apparatus facilitate repositioning side coils to provide access to biopsy plates for either medial or lateral insertion. Conventionally, repositioning a side coil from an apparatus that supported an MRI-guided breast needle biopsy required removing the side coil. Apparatus described herein are not so limited. In different embodiments a side coil may be configured to swing open to facilitate repositioning, may be configured to accordion like a bifold door, or may be configured to be repositioned in other ways. In this configuration, right side coil 840R has been moved out of the way and right side biopsy plate 820R is used to hold the breast 800L in place. FIG. 15 illustrates a front view of one embodiment of a coil 1500 that is configured to swing open like a pair of doors. Coil 1500 includes an operable portion 1520 that is configured to provide RF energy or to receive NMR signals. Operable portion 1520 may include wires, traces, circuitry, and other elements (e.g., resistor, capacitor, transistor) involved in producing RF energy used in MRI or in collecting NMR signals produced during MRI. A first hinge 1530 allows left side 1500L to swing open. A second hinge 1540 allows right side 1500R to swing open. While hinges 1530 and 1540 are described, one skilled in the art will appreciate that other devices may be employed to allow the two parts of coil 1500 to swing open. While swinging open is described, one skilled in the art will appreciate that other types of opening may be employed. Additionally, while coil 1500 is illustrated as being partitioned into two parts, a coil may be partitioned into a greater number of parts.

Coil 1500 is illustrated being split along line 1550. In this embodiment, operable portion 1520 may be configured with connectors 1520c that make electrical contact when sides 1500R and 1500L are in the shut configuration to provide continuity for a circuit or other electrical path associated with operable portion 1520. Swinging the sides 1500R and 1500L open facilitates gaining access to a biopsy plate that may be inaccessible with the sides closed. Connectors 1520c may provide continuity when the coil 1500 is shut.

Figure 16:
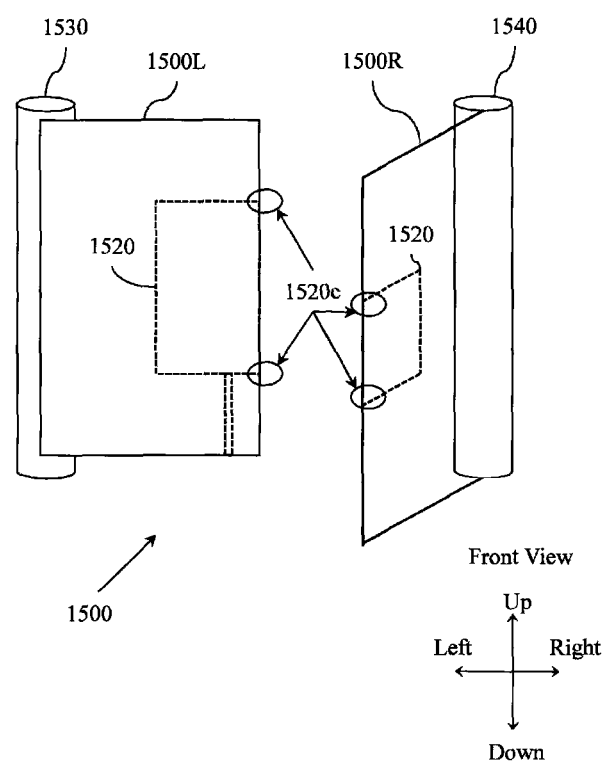
FIG. 16 illustrates a portion of an example reconfigurable MRI-guided surgical apparatus.
Figure 17:
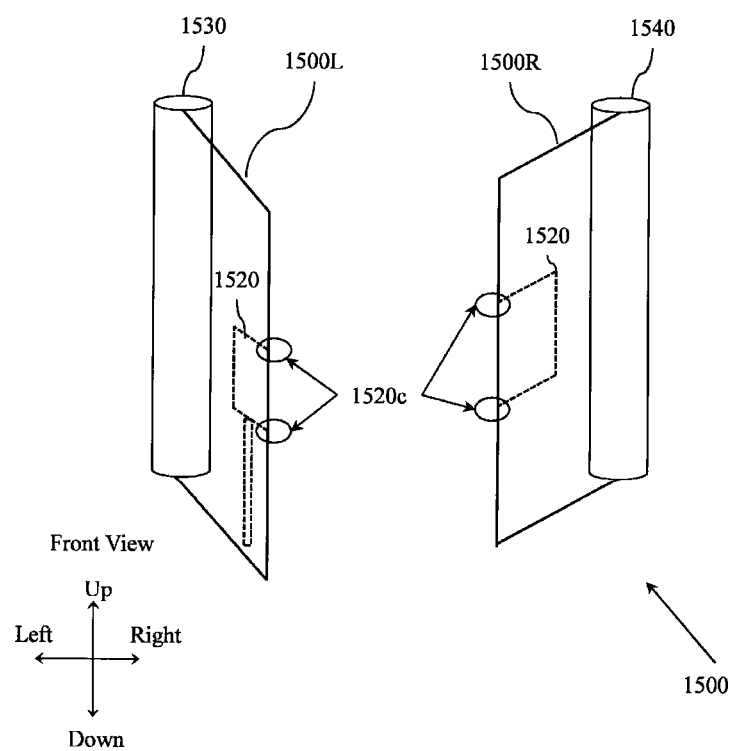
FIG. 17 illustrates a portion of an example reconfigurable MRI-guided surgical apparatus.

FIG. 16 illustrates coil 1500 with side 1500R swung partway open. Note that operable portion 1520 has been separated and that there may no longer be continuity for a circuit or other electrical pathway associated with operable portion 1520. FIG. 17 illustrates coil 1500 with side 1500L also swung partway open.

Figure 18:
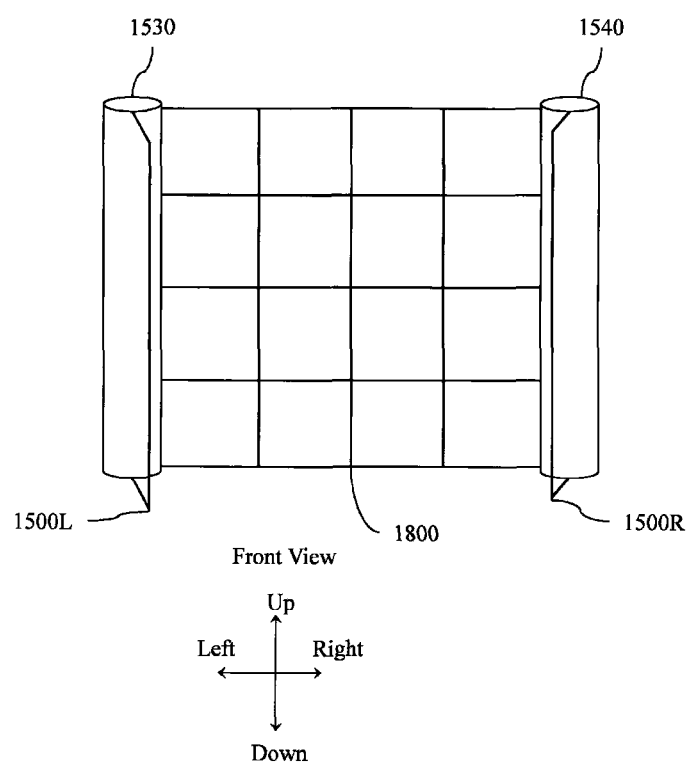
FIG. 18 illustrates a portion of an example reconfigurable MRI-guided surgical apparatus.

FIG. 18 illustrates coil 1500 with sides 1500R and 1500L swung open to reveal biopsy plate 1800. Sides 1500R and 1500L may be closed during an imaging portion of an MRI-guided needle biopsy, but then may be swung open during a biopsy portion of the procedure. The biopsy portion of the procedure may require access to biopsy plate 1800 so that a needle can be inserted into the volume (e.g., breast) being imaged and from which tissue may be harvested. Opening the portions 1500L and 1500R may be quicker than removing a side coil as is performed in conventional procedures using conventional apparatus. Additionally, leaving the separated portions of a side coil attached to a larger supporting apparatus may facilitate not misplacing the side coil and may reduce the likelihood that a side coil will be damaged or otherwise mishandled. In one embodiment, coil 1500 and biopsy plate 1800 may be located together in a single housing. In another embodiment, coil 1500 and biopsy plate 1800 may have separate housings.

Figure 19:
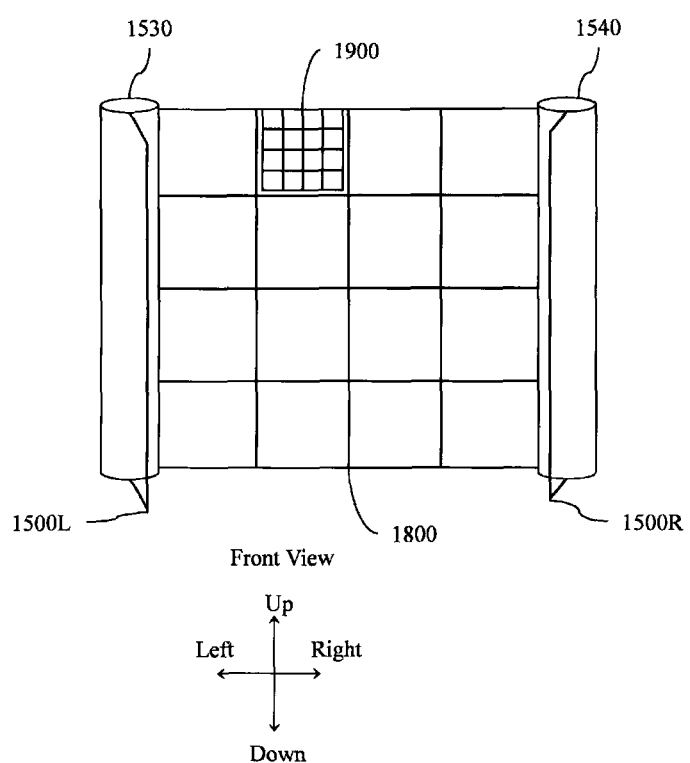
FIG. 19 illustrates a portion of an example reconfigurable MRI-guided surgical apparatus.

FIG. 19 illustrates coil 1500 with a needle positioning block 1900 inserted in biopsy plate 1800. A needle may be inserted through needle positioning block 1900 into the volume from which tissue is sought. The insertion may be precisely guided by the needle positioning block 1900. After the tissue has been harvested by the needle, the needle positioning block 1900 and biopsy plate 1800 may be removed for cleaning or disposal. A replacement biopsy plate may then be inserted into the apparatus. After the replacement biopsy plate has been inserted, the doors 1500L and 1500R may be swung shut and the apparatus prepared for another procedure.

Figure 20:
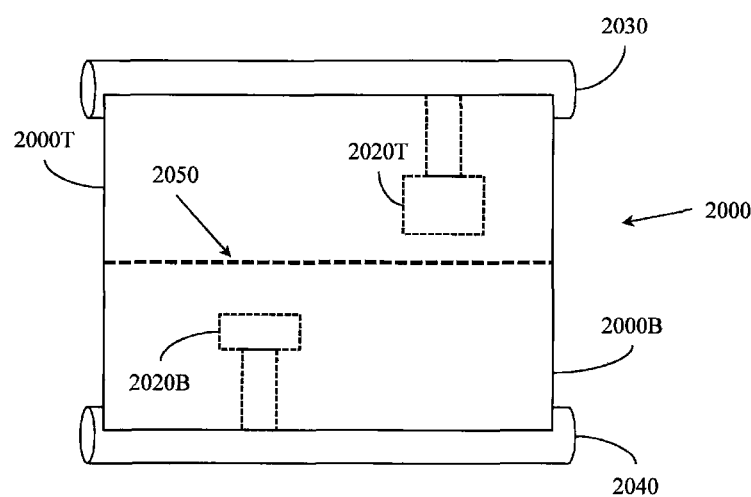
FIG. 20 illustrates a portion of an example reconfigurable MRI-guided surgical apparatus.
Figure 20:
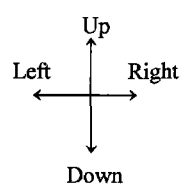

FIG. 20 illustrates a front view of a coil 2000 configured to swing open along horizontal line 2050. Coil 2000 includes a top coil 2020T and a bottom coil 2020B. Top coil 2020T may open along a path controlled by connector 2030. Connector 2030 may be, for example, a hinge. Similarly, bottom coil 2020B may open along a path controlled by connector 2040. Connector 2040 may be, for example, a hinge. In another embodiment, a single coil may span the two sides of coil 2000 (e.g., top side 2000T, bottom side 2000B). Thus, in different embodiments, side coils may be configured to open horizontally, vertically, or in other ways.

Figure 21:
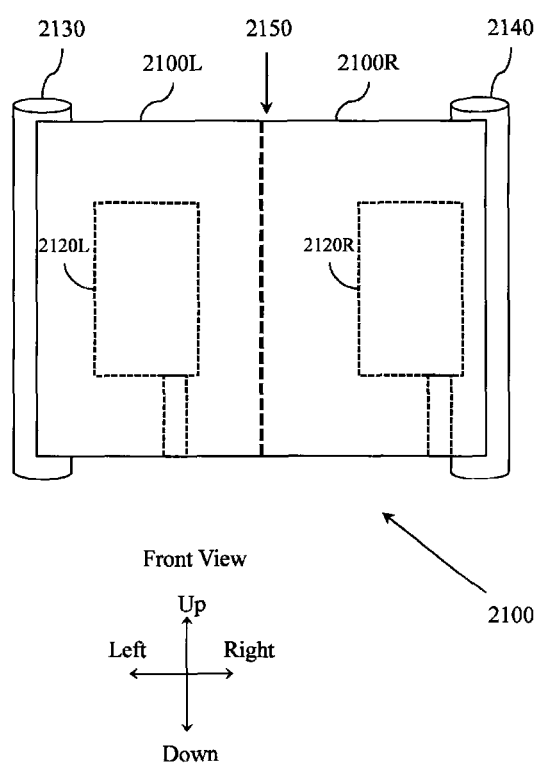
FIG. 21 illustrates a portion of an example reconfigurable MRI-guided surgical apparatus.

FIG. 21 illustrates one embodiment of a coil 2100 that is configured to swing open like a pair of folding doors. A first hinge 2130 allows left side 2100L to swing open. A second hinge 2140 allows right side 2100R to swing open. While hinges 2130 and 2140 are described, other devices may be employed to allow the two parts of coil 2100 to swing open. Additionally, while swinging open is described, other types of opening may be employed.

Coil 2100 is illustrated being split along line 2150. In this embodiment, coil 2100 may actually include two separate coils. Thus instead of coil 2100 having a single trace like copper wire 1520 (FIG. 15) for which connectors (e.g., 1520c) provided circuit continuity when the coil 1500 (FIG. 15) was in the closed configuration, coil 2100 may be configured with separate coils or traces (e.g., 2120L, 2120R). Swinging the sides 2100R and 2100L open facilitates gaining access to a biopsy plate that may be inaccessible with the sides closed.

Figure 22A:
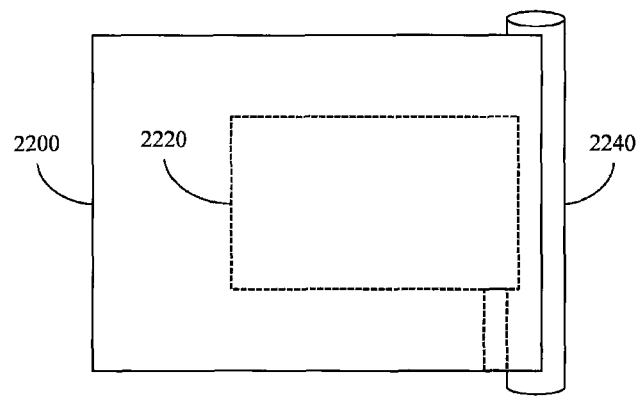
FIGS. 22a and 22b illustrate a portion of an example reconfigurable MRI-guided surgical apparatus.
Figure 22B:
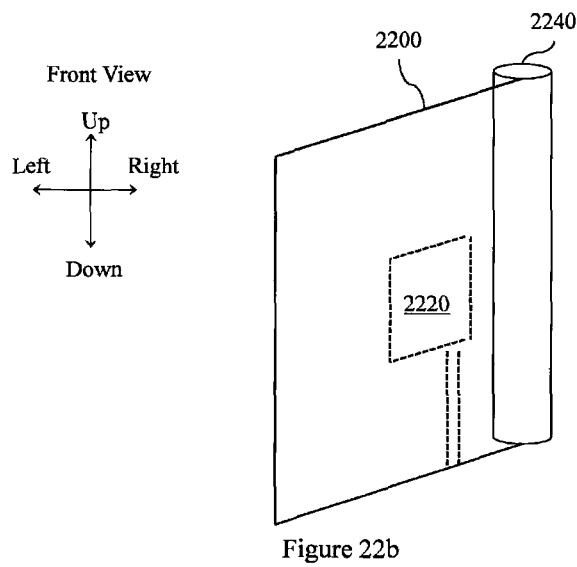

FIGS. 22a and 22b illustrate a coil 2200 mounted on a shaft 2240. Coil 2200 may be configured to rotate about shaft 2240 on the axis of shaft 2240. Coil 2200 includes operable portion 2220.

Figure 23A:
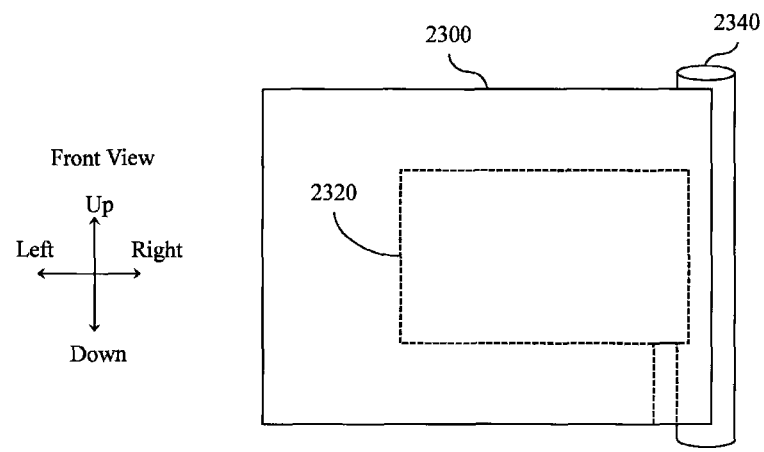
FIGS. 23a and 23b illustrate a portion of an example reconfigurable MRI-guided surgical apparatus.
Figure 23B:
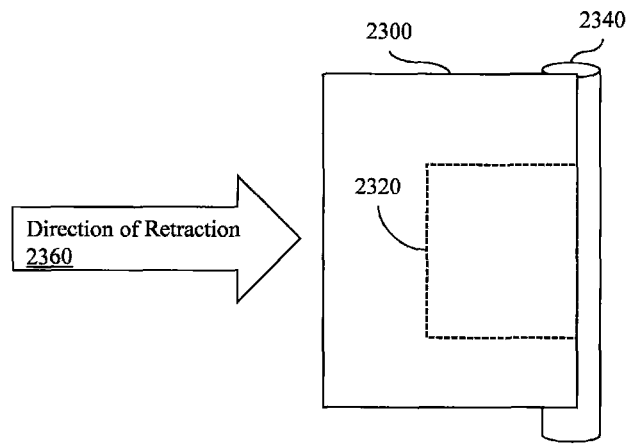

FIGS. 23a and 23b illustrate a coil 2300 that retracts like a rollup blind. Coil 2300 may include operable portion 2320 and may be retracted by a retractor 2340. To facilitate retraction, coil 2300 may be made from a material that can be rolled. While FIGS. 15-23 illustrate example ways to reposition a coil in example apparatus, a coil may repositioned in other ways in different embodiments.

In different embodiments, a biopsy plate or coil may be repositioned. The biopsy plate or coil may be movably and lockably disposed on a track, on tracks, on rail guides, or may be held by mechanical arms or other mechanical devices. In one embodiment, when multiple degrees of freedom for the biopsy plate or coil are desired, lockable joints including gimbals having several degrees of freedom may be employed. In other embodiments, a second guide rail may be mounted on or under the first rail to facilitate adjustment in multiple independent axes. In some embodiments, mechanical devices may be combined to provide both linear and rotational adjustment. In different embodiments, locking may be performed using clamps, cams, mating threads, straps, friction fits, or other mechanical immobilizers.

FIG. 24 illustrates an apparatus 2400 for use in an MRI-guided medical procedure on a patient's breast. Apparatus 2400 includes a support structure 2405 that is configured to support a patient in a face-down prone position where a breast is positioned in a first free hanging pre-imaging position. The breast would hang down through, for example, opening 2410.

Apparatus 2400 also includes an immobilization structure 2420 that is configured to facilitate repositioning the breast into an immobilized position suitable for MRI and for medical instrument access. In one embodiment, the immobilization structure 2420 includes a biopsy plate 2450, a pressure plate 2490, and at least two MRI coils. One MRI coil 2460 is positioned together with biopsy plate 2450. A second MRI coil may be positioned together with a second biopsy plate 2495. In one embodiment, pressure plate 2490 may include an RF coil. Coil 2460 may be attached to immobilization structure 2420 using a hinge 2470 that facilitates swinging coil 2460 away from biopsy plate 2450 to provide access to biopsy plate 2450.

In one embodiment, an MRI coil is configured to be repositioned from a first position associated with the free hanging pre-imaging position to a second position associated with the immobilized position. Repositioning the MRI coil facilitates improving SNR by placing the coil closer to the breast being imaged. Thus, the SNR associated with signal received from the breast through the MRI coil is improved by repositioning the coil from the first position to the second position. Since the breast is being imaged as part of an MRI-guided procedure (e.g., needle biopsy), the immobilization structure 2420 is configured to allow removal of the biopsy plate 2450 without removing an MRI coil. This will be illustrated in more detail in FIG. 25. The immobilized position may be achieved by moving biopsy plate 2450 towards pressure plate 2490 in an amount sufficient to trap a breast hanging down between the biopsy plate 2450 and the pressure plate 2490. A force sufficient to immobilize the trapped breast may be applied.

In one embodiment, the immobilization structure 2420 is configured to hold MRI coils parallel to each other in a position suitable for performing bilateral imaging when the breast is held in the immobilized position. Holding MRI coils parallel may be achieved by, for example, configuring immobilization structure 2420 with rails 2430 upon which the MRI coils may slide. Rails 2430 may also be used to mount, move, and lock in place the biopsy plate 2450. While rails 2430 are described, other structures (e.g., tracks, guides) may be employed to hold the MRI coils in a parallel position and to allow the MRI coils to move towards and away from a breast.

In one embodiment, the immobilization structure 2420 is configured to hold MRI coils perpendicular to each other in a position suitable for performing unilateral imaging when the breast is held in the immobilized position. This may include rotating an MRI coil from an upright position that is parallel to another MRI coil to a flat position. Thus, immobilization structure 2420 may be configured with a joint that facilitates repositioning a coil from the upright position to the flat position. When the two coils are perpendicular to each other, unilateral imaging may be performed using high resolution imaging. When high resolution imaging is employed, an SNR associated with signal received from the breast through the MRI coils during unilateral imaging may be superior to an SNR associated with signal received from the breast through the MRI coils during bilateral imaging.

Figure 25:
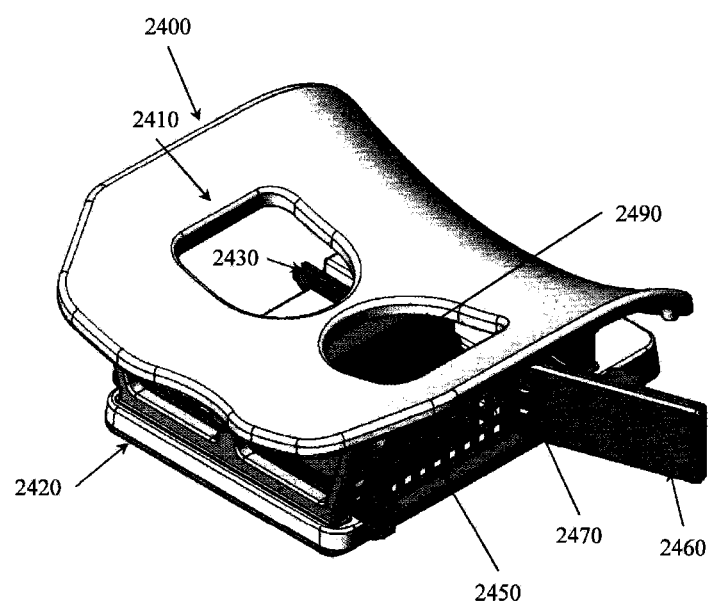
FIG. 25 illustrates an example reconfigurable MRI-guided surgical apparatus.

FIG. 25 illustrates apparatus 2400 with the MRI coil 2460 rotated away from biopsy plate 2450. In this open configuration, biopsy plate 2450 may be accessed to facilitate applying a medical instrument (e.g., biopsy needle) through biopsy plate 2450 to reach a breast positioned between biopsy plate 2450 and pressure plate 2490.

Figure 26:
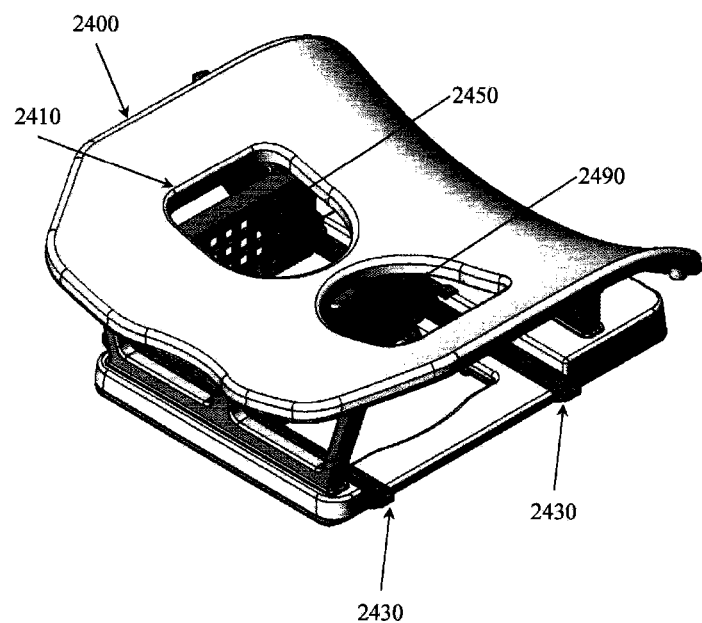
FIG. 26 illustrates an example reconfigurable MRI-guided surgical apparatus.

FIG. 26 illustrates apparatus 2400 from a different viewpoint. In this view, rails 2430 are more clearly visible. While FIGS. 24-26 illustrate one example model, FIGS. 27-34 illustrate various component parts of an inner assembly being reconfigured during the lifecycle of an MRI-guided medical procedure.

Figure 27:
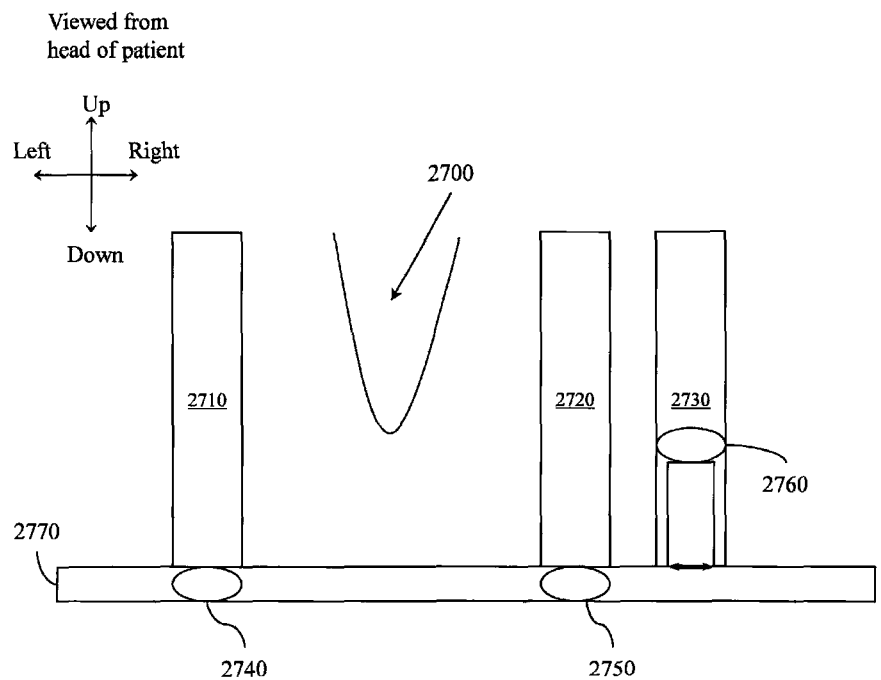
FIG. 27 illustrates a portion of an example reconfigurable MRI-guided surgical apparatus.

FIG. 27 illustrates a portion of an inner assembly for use with a breast coil in an MRI-guided medical procedure on a patient's breast. FIG. 27 illustrates a breast 2700 disposed between a brace assembly 2710 and a medical instrument guidance assembly 2720. The medical instrument guidance assembly 2720 is attached to a guide 2770 by a connector 2750. The brace assembly 2710 is attached to the guide 2770 by a rotation point 2740. The breast 2700 is also disposed between the brace assembly 2710 and a side coil 2730. The side coil 2730 includes a hinge 2760. In one embodiment, guide 2770 may correspond to rails 2430 (FIG. 26).

The side coil 2730 is configured to participate in MRI of the breast 2700. Thus, in different embodiments, the side coil 2730 may be configured to generate RF energy to be applied to the breast 2700 during the MRI-guided medical procedure and/or may be configured to receive NMR signals from the breast 2700 during the MRI-guided medical procedure.

The medical instrument guidance assembly 2720 is configured to contact the breast 2700. The medical instrument guidance assembly 2720 is also configured to be inserted into and removed from a larger apparatus (e.g., breast coil) housing the inner assembly without removing the side coil 2730. In one embodiment, the medical instrument guidance assembly 2720 may correspond to biopsy plate 2450 (FIG. 25) and the larger apparatus may correspond to breast coil 2400.

The brace assembly 2710 is also configured to contact the breast 2700. For example, the medical instrument guidance assembly 2720 could be moved to the left to contact breast 2700 from one side and the brace assembly 2710 could be moved to the right to contact breast 2700 from the opposite side. Alternatively, the entire assembly could be moved to the right until brace assembly 2710 was in contact with breast 2700 and then the medical instrument guidance assembly 2720 could be moved to the left to contact breast 2700. Other movements may also be employed.

Guide 2770 is configured to movably and lockably position the medical instrument guidance assembly 2720, the side coil 2730, and the brace assembly 2710 in both an imaging mode and a procedure mode. Being configured to "movably and lockably position" an item means that guide 2770 can be used to facilitate moving the item from a first position to a second position and fixing the item at either position. The movement may be guided by rails, for example. The locking may be performed by a clamp, for example. Thus, the medical instrument guidance assembly 2720, the side coil 2730, and the brace assembly 2710 may be movably engaged to the guide 2770. In one embodiment, the guide 2770 may be configured for positioning the medical instrument guidance assembly 2720 on a first side of the breast 2700 and for positioning the brace assembly 2710 on a second, opposing side of the breast 2700 so that the assembly 2710 and assembly 2720 can be used to apply to the breast 2700 a force sufficient to hold the breast 2700 against the medical instrument guidance assembly 2720 in a fixed spatial relationship having a desired tolerance during the MRI-guided medical procedure. The tolerance may be, for example, one millimeter.

The guide 2770 may be configured with a connector 2750 for removably attaching the medical instrument guidance assembly 2720. In different embodiments, different types of connectors may be employed.

The guide 2770 may be configured to control and allow movement of the side coil 2730 from a first position to a second position. Being configured to "control and allow movement" of an item means that guide 2770 can provide the mechanical structure (e.g., rails) that allow an item to move back and forth and that also define the possible positions to which the item can be moved. In one example, the first position may be farther from the breast 2700 and the second position may be closer to the breast 2700. Thus, a signal received from the breast 2700 by the side coil 2730 in the first position during the MRI-guided surgical procedure may yield a first SNR and a signal received from the breast 2700 by the side coil 2730 in the second position during the MRI-guided surgical procedure may yield a second, higher SNR.

In one embodiment, the guide 2770 may be configured with a hinge 2760 to control and allow movement of the side coil 2730 to a third position. The third position may facilitate accessing the medical instrument guidance assembly 2720 for a medical instrument to be inserted into the breast through the medical instrument guidance assembly 2720.

In one embodiment, the medical instrument guidance assembly 2720 may be a biopsy plate and the medical instrument may be a needle suitable for performing a needle biopsy. Since access from either side of breast 2700 may be desired, in one embodiment, the brace assembly 2710 may include a second medical instrument guidance assembly and a second side coil.

Figure 28:
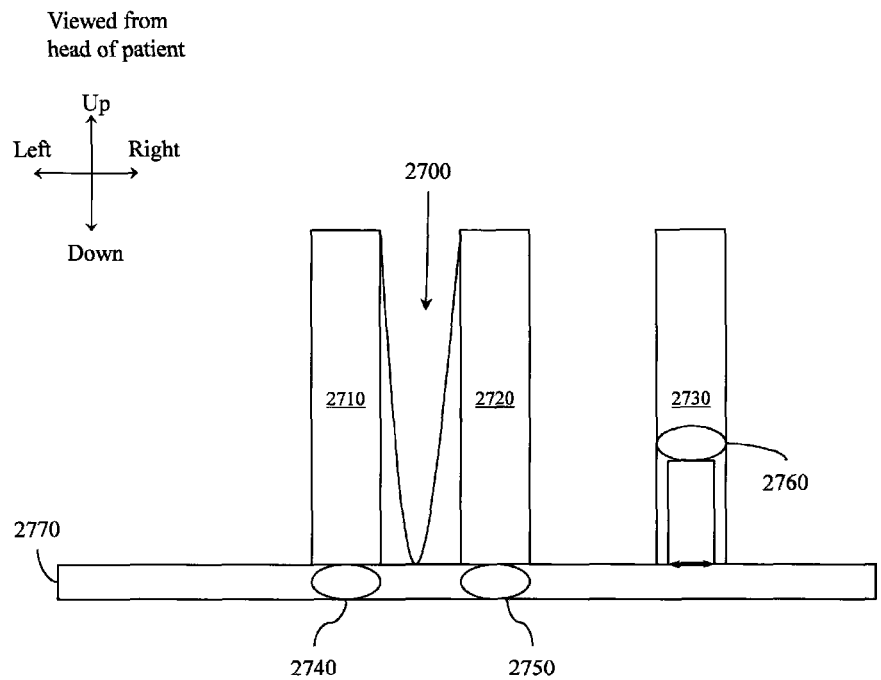
FIG. 28 illustrates a portion of an example reconfigurable MRI-guided surgical apparatus.

FIG. 28 illustrates the breast 2700 after it has been contacted and immobilized by the brace assembly 2710 and the medical instrument guidance assembly 2720. The brace assembly 2710 and the medical instrument guidance assembly 2720 cooperate to apply a force sufficient to immobilize breast 2700 to within a desired tolerance. In one embodiment, the tolerance may be less than 1 millimeter of movement throughout the medical procedure.

Figure 29:
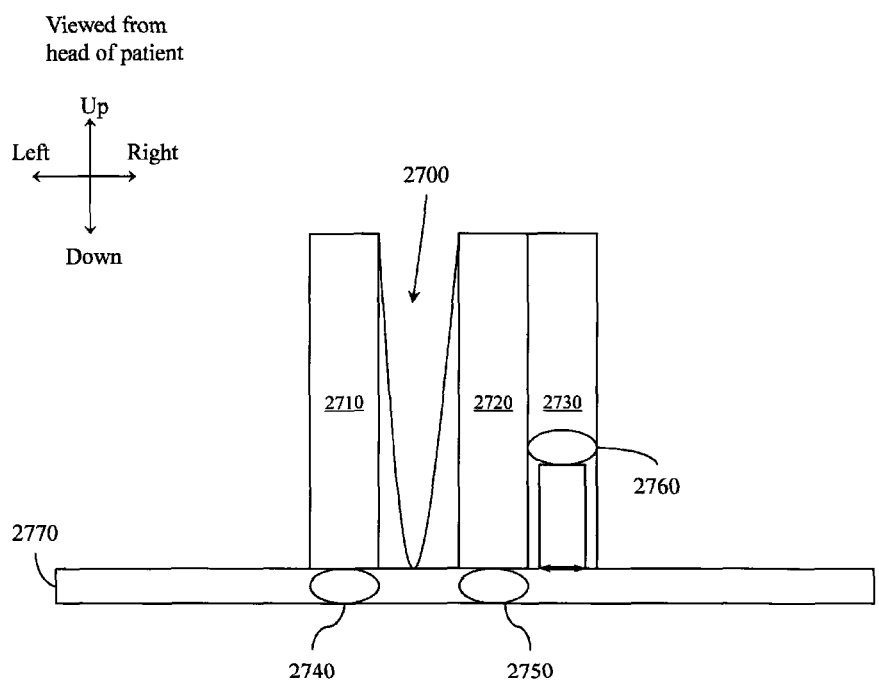
FIG. 29 illustrates a portion of an example reconfigurable MRI-guided surgical apparatus.

FIG. 29 illustrates side coil 2730 after it has been moved closer to breast 2700. The SNR of a signal received from breast 2700 will likely be higher when side coil 2730 is closer to breast 2730 as illustrated in FIG. 29 than it would be when the side coil 2730 is farther from breast 2730 as illustrated in FIG. 28.

Figure 30:
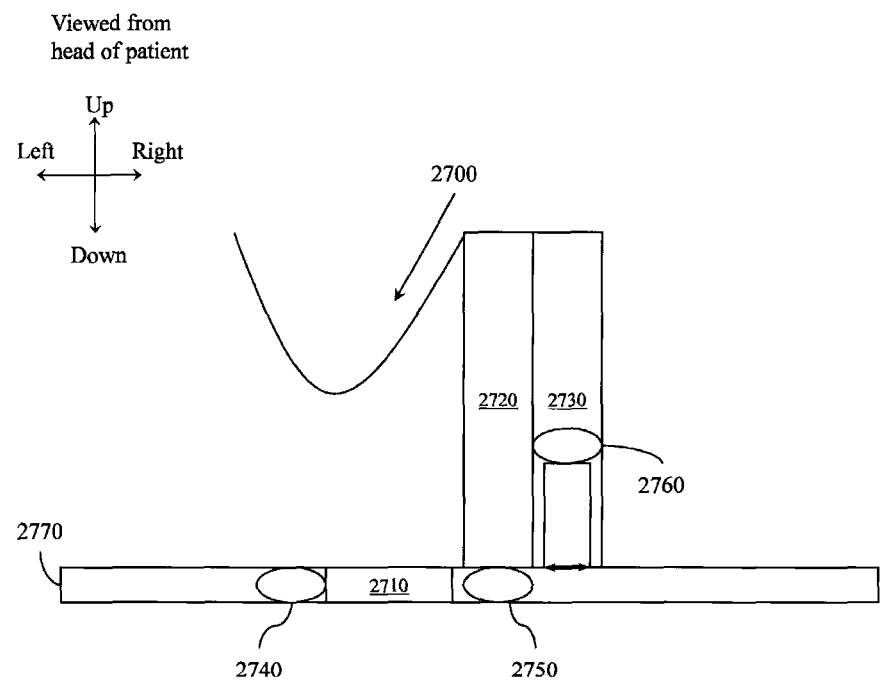
FIG. 30 illustrates a portion of an example reconfigurable MRI-guided surgical apparatus.

FIG. 30 illustrates brace assembly 2710 after it has been rotated from its original position to a subsequent position. In one embodiment, the guide 2770 may be configured with a rotation point 2740 to control and allow movement of the brace assembly 2710 from the original position to the subsequent position. The first position may be used for bilateral imaging and the subsequent position may be used for unilateral imaging. The rotation point 2740 may be, for example, a hinge, a gimbal, or other device that permits rotation or relocation from the upright position illustrated in FIG. 29 to the horizontal position illustrated in FIG. 30. While a perfectly vertical orientation for brace assembly 2710 is illustrated in FIG. 29, and while a perfectly horizontal orientation is illustrated for brace 2710 in FIG. 30, guide 2770 and rotation point 2740 may be configured to produce other orientations for brace assembly 2710. This configuration illustrates an intermediate position before the breast 2700 has been compressed between the two sides.

Figure 31:
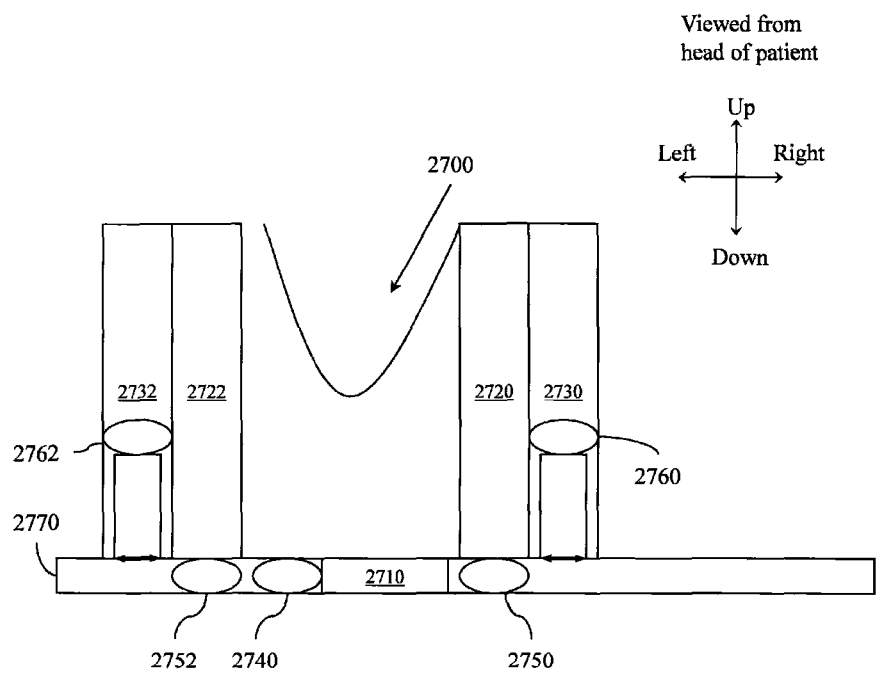
FIG. 31 illustrates a portion of an example reconfigurable MRI-guided surgical apparatus.

FIG. 31 illustrates the inner assembly configured with a second medical instrument guidance assembly 2722 and a second side coil 2732. In this embodiment, the guide 2770 may be configured to movably and lockably position the second medical instrument guidance assembly 2722 in both the imaging mode and the procedure mode. Thus, the second medical instrument guidance assembly 2722 may be movably engaged to the guide 2770. The guide 2770 may be configured with a second connector 2752 for removably attaching the second medical instrument guidance assembly 2722 to the guide 2770.

In this embodiment, the guide 2770 may be configured for positioning the second medical instrument guidance assembly 2722 on the second, opposing side of the breast 2700 to facilitate applying to the breast 2700 a force sufficient to hold the breast 2700 against the medical instrument guidance assembly 2720 and the second medical instrument guidance assembly 2722 in a fixed spatial relationship having a desired tolerance during the MRI-guided medical procedure.

FIG. 31 also illustrates the second side coil 2732. The guide 2770 is configured to facilitate moving and locking the second side coil 2732 in position in both the imaging mode and the procedure mode. The guide 2770 is configured to control and allow movement of the second side coil 2732 from an initial position to a subsequent position. Moving second side coil 2732 facilitates having a signal received from the breast 2700 by the second side coil 2732 in the initial position during the MRI-guided surgical procedure yield an initial SNR, and having a signal received from breast 2700 by the second side coil 2732 in the subsequent position during the MRI-guided surgical procedure have a higher SNR.

In different embodiments, the guide 2770 may be configured with a second hinge 2762 to control and allow movement of the second side coil 2732 to an open position that provides access to the second medical instrument guidance assembly 2722 for the medical instrument to be inserted into the breast 2700 through the second medical instrument guidance assembly 2722.

Figure 32:
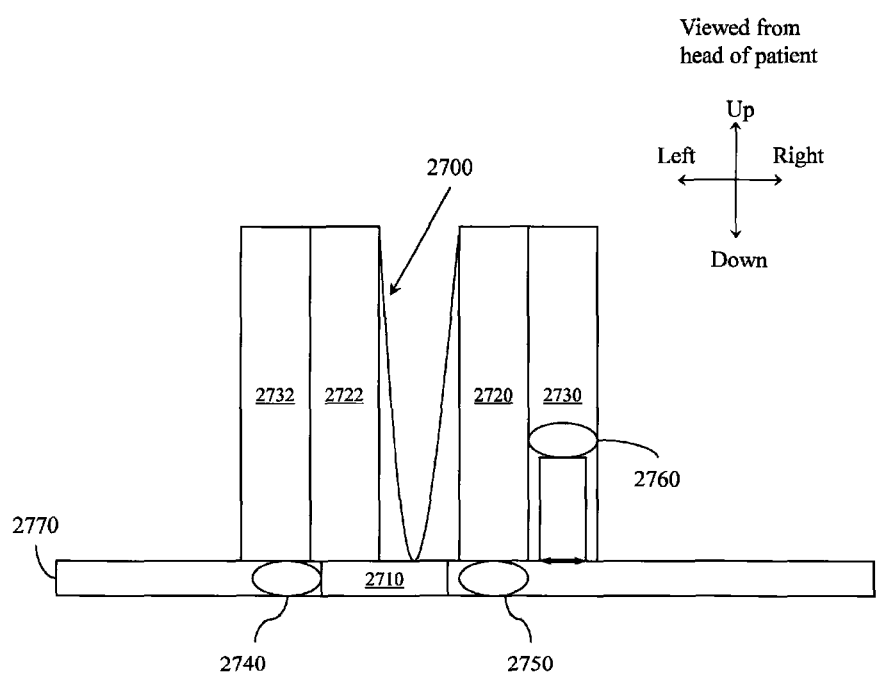
FIG. 32 illustrates a portion of an example reconfigurable MRI-guided surgical apparatus.

FIG. 32 illustrates how the guide 2770 can be configured to facilitate switching from bilateral imaging to unilateral imaging during an MRI-guided procedure. The switching is possible when the guide 2770 is configured to control and allow repositioning (e.g., rotation) of the brace assembly 2710 from a vertical position used in bilateral imaging to a horizontal position used in unilateral imaging. As described above, the rotation or other repositioning of assembly 2710 is accomplished by rotation point 2740.

With the brace assembly 2710 in the horizontal position, a breast coil housing the inner assembly may be configured to perform quadrature imaging using at least one of the side coils 2730 and 2732 and a coil in the brace assembly 2710 when positioned perpendicular to the at least one side coil.

In one embodiment, the guide 2770 may be configured to hold the medical instrument guidance assembly 2720, the brace assembly 2710, and the side coil 2730 in a set of parallel planes. In another embodiment, the guide 2770 may be configured to hold the medical instrument guidance assembly 2720, the second medical instrument guidance assembly 2722, the side coil 2730, the second side coil 2732, and the brace assembly 2710 in a set of parallel planes.

In different embodiments, the guide 2770 may also be configured to hold the brace assembly 2710 in a position perpendicular to the medical instrument guidance assembly 2720, the side coil 2730, the second medical instrument guidance assembly 2732, or the second side coil 2732.

The inner assembly illustrated in FIGS. 27-32 may be positioned in a breast coil having a top portion and a bottom portion as illustrated in FIGS. 24-26. In different embodiments, the top portion may be configured with one or more coils positioned and configured for performing MRI of the breast and the bottom portion may also be configured with one or more coils positioned and configured for performing MRI of the breast.

Figure 33:
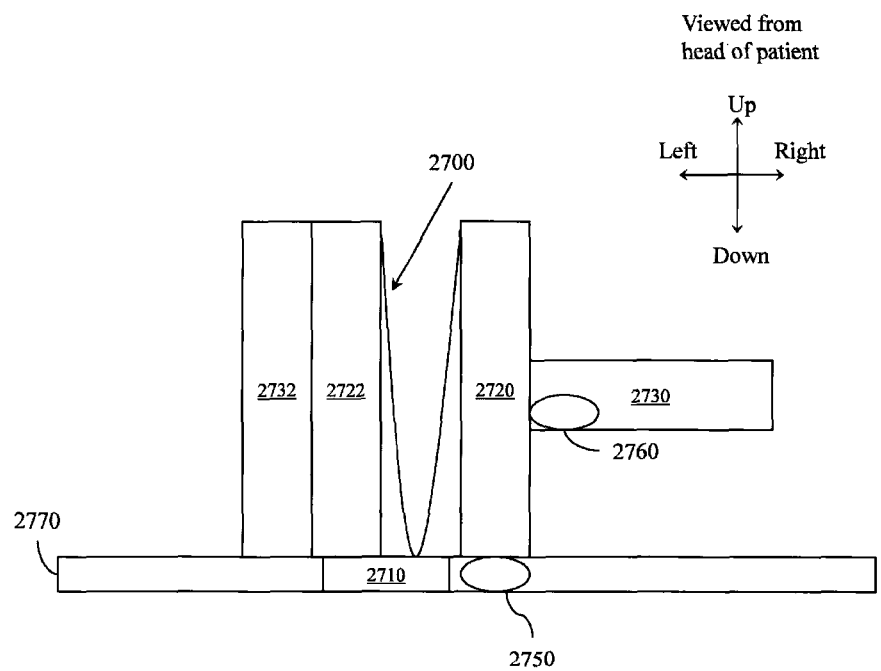
FIG. 33 illustrates a portion of an example reconfigurable MRI-guided surgical apparatus.
Figure 34:
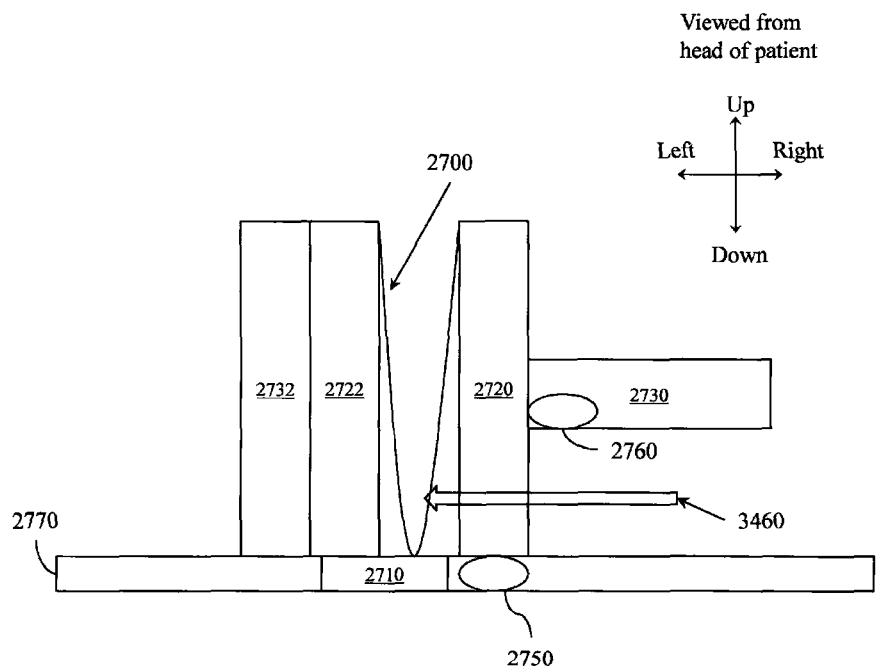
FIG. 34 illustrates a portion of an example reconfigurable MRI-guided surgical apparatus.
Figure 35:
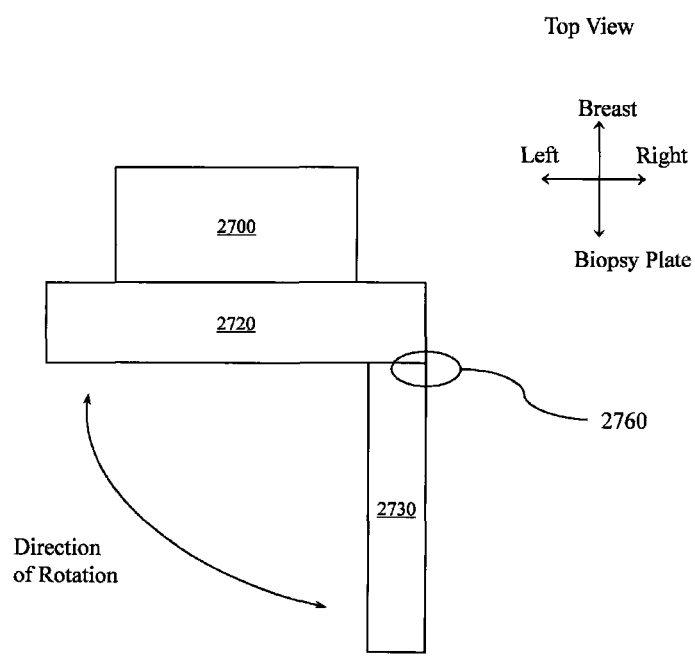
FIG. 35 illustrates a portion of an example reconfigurable MRI-guided surgical apparatus.
Figure 36:
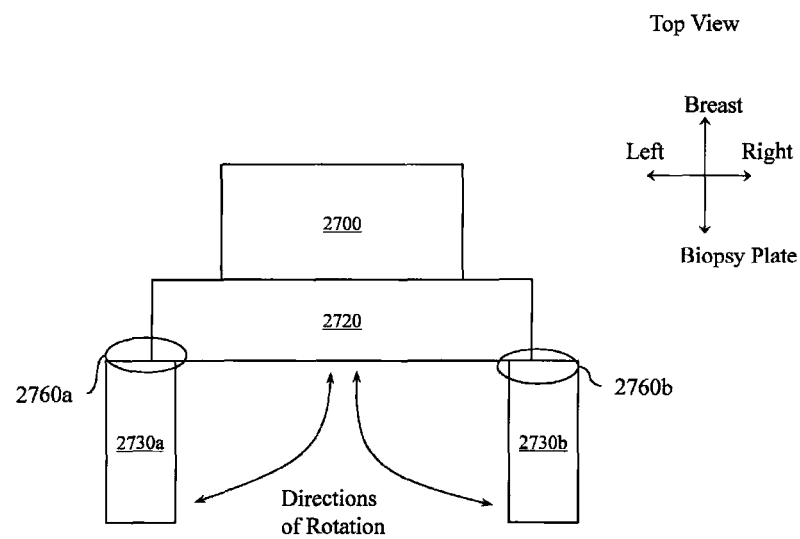
FIG. 36 illustrates a portion of an example reconfigurable MRI-guided surgical apparatus.
Figure 37:
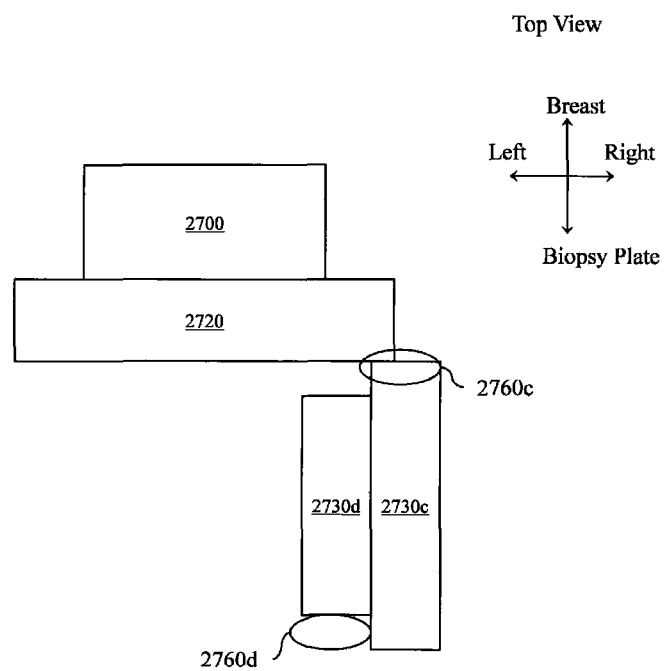
FIG. 37 illustrates a portion of an example reconfigurable MRI-guided surgical apparatus.

FIG. 33 illustrates the side coil 2730 having been moved to facilitate accessing breast 2700 via medical instrument guidance assembly 2720. In this embodiment, side coil 2730 has been rotated about an axis defined by hinge 2760. Other possible movements are illustrated in FIGS. 35-37. FIG. 34 illustrates breast 2700 with a needle 3460 inserted via medical instrument guidance assembly 2720.

FIG. 35 illustrates the hinge 2760 being configured to facilitate swinging the side coil 2730 away from the medical instrument guidance assembly 2720 as a single piece on a single axis. Swinging side coil 2730 away from medical instrument guidance assembly 2720 facilitates accessing breast 2700 without removing coil 2730.

FIG. 36 illustrates the side coil 2730 repositioned away from the medical instrument guidance assembly 2720. Side coil 2730 has been moved as two pieces on two axes. In this embodiment, guide 2770 may be configured with two hinges 2760*a* and 2760*b* and side coil 2730 may be split into pieces 2730*a* and 2730*b*.

FIG. 37 illustrates the side coil 2730 repositioned away from the medical instrument guidance assembly 2720. Side coil 2730 has been moved as two pieces. In this embodiment, guide 2770 may be configured with a single hinge 2760*c* and side coil 2730 may be configured with an additional hinge 2760*d*. In this embodiment, side coil 2730 may be split into two pieces 2730*c* and 2730*d*.

Figure 38:
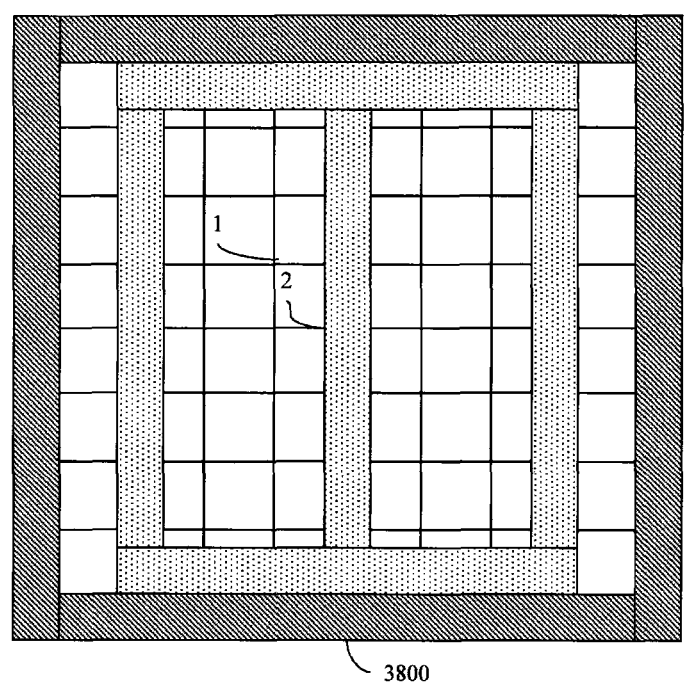
FIG. 38 illustrates a biopsy plate in a frame with a slideable coil.
Figure 38:
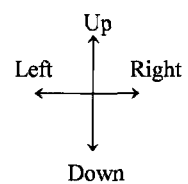

FIG. 38 illustrates a frame 3800 that houses a biopsy plate 1 and a coil 2. Frame 3800, coil 2, and biopsy plate 1 are configured to facilitate acquiring an MR image of an object. Frame 3800, coil 2, and biopsy plate 1 are also configured to facilitate positioning a needle during an MRI guided procedure. In one embodiment, the needle can be placed without having to move the coil 2. In one embodiment, the coil 2 may have openings that facilitate accessing biopsy plate 1. In one embodiment, both coil 2 and biopsy plate 1 may be housed in the same frame 3800. Coil 2 and biopsy plate 1 may have different sizes. For example, coil 2 may be larger than biopsy plate 1, may be the same size as biopsy plate 1, or may be smaller than biopsy plate 1. Similarly, coil 2 and frame 3800 may have different sizes. For example, coil 2 may be larger than frame 3800, may be the same size as frame 3800, or may be smaller than frame 3800. Even if the coil 2 has openings or is smaller than the frame 3800, portions of coil 2 may block access to portions of biopsy plate 1.

Figure 39:
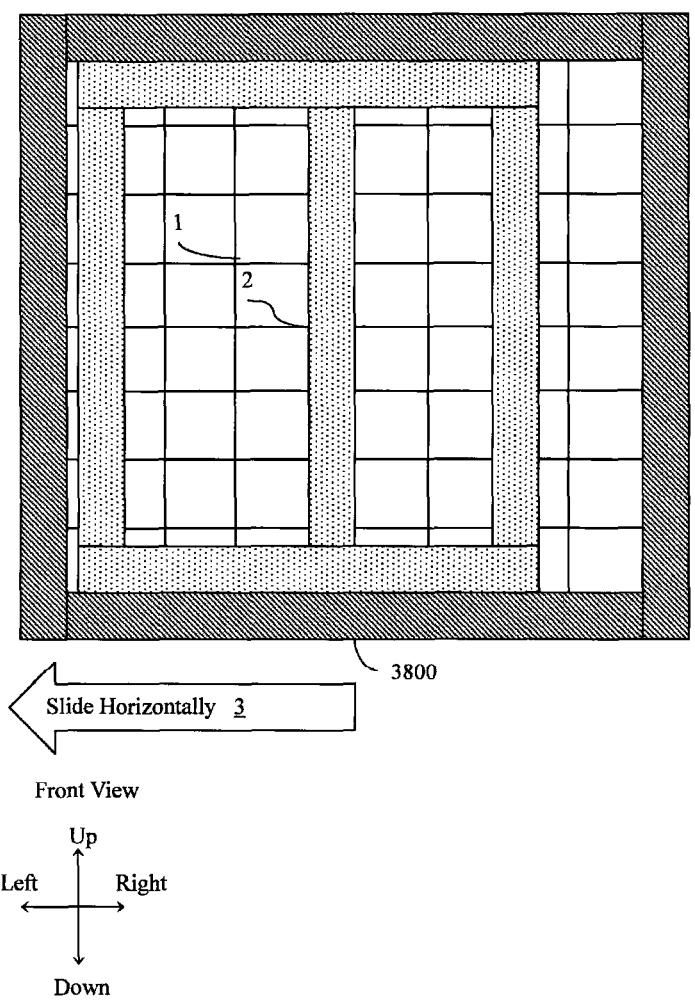
FIG. 39 illustrates a biopsy plate in a frame with a slideable coil.

Therefore, FIG. 39 illustrates frame 3800 with coil 2 after it has been displaced in the horizontal direction indicated by arrow 3. In one embodiment, the coil 2 may be able to be slid left to right in frame 3800. In another embodiment, the coil 2 may be able to be slid up and down in frame 3800. In another embodiment, coil 2 may be able to be rotated in frame 3800.

More generally, a portion of an inner assembly may include an apparatus that includes a frame or other support configured to hold a biopsy plate and a coil in a position that facilitates acquiring an MR image during an MRI-guided procedure. The coil may be configured to allow access to the biopsy plate while the coil is in place. Additionally, the frame or other support may be configured to allow the coil to be repositioned yet still remain in a position from which the coil can function to acquire an image during the MRI-guided procedure.

In one embodiment, an example apparatus for use in a magnetic resonance imaging (MRI) guided medical procedure on a patient's breast includes a support structure configured to support a patient in a face-down prone position. A breast of the patient is positioned in a first free hanging pre-imaging position. The example apparatus also includes an immobilization structure configured to reposition the breast into an immobilized position suitable for MRI and for medical instrument access.

In one example, the immobilization structure includes a biopsy plate, a pressure plate, and an MRI coil. The MRI coil may be configured to be repositioned from a first position associated with the free hanging pre-imaging position to a second position associated with the immobilized position, where a signal to noise ratio (SNR) associated with signal received from the breast through the MRI coil is improved by repositioning the coil from the first position to the second position.

In one embodiment, the coil is configured with an opening sufficient to allow access to the breast through the biopsy plate through the MRI coil.

In one embodiment, the coil is movable from an initial position to a subsequent position so that a portion of the biopsy plate that is inaccessible while the coil is in the initial position is accessible while the coil is in the subsequent position. An MR image of the breast can be acquired with the coil in either of the initial position or the subsequent position.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

An "operable connection", or a connection by which entities are "operably connected", is one in which signals, physical communications, and/or logical communications may be sent and/or received. An operable connection may include a physical interface, an electrical interface, and/or a data interface. An operable connection may include differing combinations of interfaces and/or connections sufficient to allow operable control. For example, two entities can be operably connected to communicate signals to each other directly or through one or more intermediate entities (e.g., processor, operating system, logic, software). Logical and/or physical communication channels can be used to create an operable connection.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one of, A, B, and C" is employed herein, (e.g., a data store configured to store one of, A, B, and C) it is intended to convey the set of possibilities A, B, C, AB, AC, BC, or ABC (e.g., the data store may store only A, only B, only C, A&B, A&C, B&C, or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

To the extent that the phrase "one or more of, A, B, and C" is employed herein, (e.g., a data store configured to store one or more of, A, B, and C) it is intended to convey the set of possibilities A, B, C, AB, AC, BC, ABC, AA . . . A, BB . . . B, CC . . . C, AA . . . ABB . . . B, AA . . . ACC . . . C, BB . . . BCC . . . C, or AA . . . ABB . . . BCC . . . C (e.g., the data store may store only A, only B, only C, A&B, A&C, B&C, A&B&C, or other combinations thereof). It is not intended to require one of A, one of B, and one of C. When the applicants intend to indicate "at least one of A, at least one of B, and at least one of C", then the phrasing "at least one of A, at least one of B, and at least one of C" will be employed.

What is claimed is:

1. An inner assembly for use with a breast coil in a magnetic resonance imaging (MRI) guided medical procedure on a patient's breast, the inner assembly comprising:
   a side coil configured to participate in MRI of the breast;
   a medical instrument guidance assembly configured to contact the breast, the medical instrument guidance assembly being configured to be inserted into and removed from the inner assembly without removing the side coil from the inner assembly, the medical instrument guidance assembly being a biopsy block, the biopsy block being configured to hold a needle positioning block;
   a brace assembly configured to contact the breast; and
   a guide configured to movably and lockably position the medical instrument guidance assembly, the side coil, and the brace assembly in both an imaging mode and a biopsy mode,
   the medical instrument guidance assembly, the side coil, and the brace assembly being movably engaged to the guide,
   the guide being configured with a connector for removably attaching the medical instrument guidance assembly to the inner assembly,
   the guide being configured for positioning the medical instrument guidance assembly on a first side of the breast and for positioning the brace assembly on a second, opposing side of the breast to facilitate applying to the breast a force sufficient to hold the breast against the medical instrument guidance assembly in a fixed spatial relationship having a desired tolerance during the MRI-guided medical procedure,
   the guide being configured to control and allow movement of the side coil from a first position to a second position, where a signal received from the breast by the side coil in the first position during the MRI-guided surgical procedure yields a first signal to noise ratio (SNR), and where a signal received from the breast by the side coil in the second position during the MRI-guided surgical procedure yields a second, higher SNR,
   the guide being configured with a hinge configured to control and allow movement of the side coil to a third position, where the third position provides access to the medical instrument guidance assembly for a medical instrument configured to be inserted into the breast through the medical instrument guidance assembly, the medical instrument being a needle suitable for performing a needle biopsy,
   the guide being configured with a rotation point configured to control and allow movement of the brace assembly from a first position used for bilateral imaging to a second position used for unilateral imaging,
   where the needle positioning block controls, at least in part, a position and direction of travel of the medical instrument during the biopsy mode.

2. The inner assembly of claim 1, the brace assembly comprising a second medical instrument guidance assembly and a second side coil.

3. The inner assembly of claim 1, the side coil being configured to generate radio frequency (RF) energy to be applied to the breast during the MRI-guided medical procedure.

4. The inner assembly of claim 1, the side coil being configured to receive nuclear magnetic resonance (NMR) signals from the breast during the MRI-guided medical procedure.

5. The inner assembly of claim 1, comprising a second medical instrument guidance assembly,
   the guide being configured to movably and lockably position the second medical instrument guidance assembly in both the imaging mode and the biopsy mode,
   the second medical instrument guidance assembly being movably engaged to the guide,
   the guide being configured with a second connector for removably attaching the second medical instrument guidance assembly to the apparatus,
   the guide being configured for positioning the second medical instrument guidance assembly on the second, opposing side of the breast to facilitate applying to the breast a force sufficient to hold the breast against the medical instrument guidance assembly in a fixed spatial relationship having a desired tolerance during the MRI-guided medical procedure.

6. The inner assembly of claim 5, comprising a second side coil,
   the guide being configured to movably and lockably position the second side coil in both the imaging mode and the biopsy mode,
   the guide being configured to control and allow movement of the second side coil from an initial position to a subsequent position, where a signal received from the breast by the second side coil in the initial position during the MRI-guided surgical procedure yields an initial SNR, and where a signal received from the breast by the second side coil in the subsequent position during the MRI-guided surgical procedure yields a subsequent, higher SNR, the guide being configured with a second hinge to control and allow movement of the second side coil to an open position, where the open position provides access to the second medical instrument guidance assembly for the medical instrument to be inserted into the breast through the second medical instrument guidance assembly.

7. The inner assembly of claim 6, the guide being configured to facilitate switching the MRI-guided medical procedure from bilateral imaging to unilateral imaging by controlling and allowing rotation of the brace assembly from a vertical position used in bilateral imaging to a horizontal position used in unilateral imaging,
   the guide being configured to facilitate repositioning the second medical instrument guidance assembly to contact the breast to be imaged for unilateral imaging.

8. The inner assembly of claim 6, the guide being configured to hold the medical instrument guidance assembly, the second medical instrument guidance assembly, the side coil, the second side coil, and the brace assembly in a set of parallel planes.

9. The inner assembly of claim 1, the breast coil being, configured to perform high resolution imaging using at least one of the side coils and a coil in the brace assembly when the coil in the brace assembly is positioned perpendicular to the at least one side coil.

10. The inner assembly of claim 1, the guide being configured to hold the medical instrument guidance assembly, the brace assembly, and the side coil parallel to each other.

11. The inner assembly of claim 1, the guide being configured to hold the brace assembly in a position perpendicular to the medical instrument guidance assembly.

12. The inner assembly of claim 1, comprising a top portion and a bottom portion, the top portion being configured with one or more coils positioned and configured for performing MRI of the breast, the bottom portion being configured with one or more coils positioned and configured for performing MRI of the breast.

13. The inner assembly of claim 1, the hinge being configured to facilitate swinging the side coil away from the medical instrument guidance assembly as a single piece on a single axis.

14. The inner assembly of claim 1, the side coil comprising two pieces, the hinge being configured to facilitate moving the side coil away from the medical instrument guidance assembly as two or more pieces on two or more axes.

15. The inner assembly of claim 1, the tolerance being one millimeter.

\* \* \* \* \*